US010953228B2

(12) United States Patent
Perryman et al.

(10) Patent No.: US 10,953,228 B2
(45) Date of Patent: *Mar. 23, 2021

(54) IMPLANTABLE LEAD

(71) Applicant: Stimwave Technologies Incorporated, Fort Lauderdale, FL (US)

(72) Inventors: Laura Tyler Perryman, Miami Beach, FL (US); Patrick Larson, Surfside, FL (US); Chad Andresen, Miami Beach, FL (US)

(73) Assignee: Stimwave Technologies Incorporated, Pompano Beach, FL (US)

( * ) Notice: Subject to any disclaimer, the term of this patent is extended or adjusted under 35 U.S.C. 154(b) by 19 days.

This patent is subject to a terminal disclaimer.

(21) Appl. No.: 16/275,666

(22) Filed: Feb. 14, 2019

(65) Prior Publication Data
US 2019/0247660 A1    Aug. 15, 2019

Related U.S. Application Data

(63) Continuation of application No. 15/709,962, filed on Sep. 20, 2017, now Pat. No. 10,238,874, which is a
(Continued)

(51) Int. Cl.
*A61N 1/36* (2006.01)
*A61N 1/05* (2006.01)
(Continued)

(52) U.S. Cl.
CPC ....... *A61N 1/36071* (2013.01); *A61N 1/0551* (2013.01); *A61N 1/3787* (2013.01);
(Continued)

(58) Field of Classification Search
USPC .................................................. 607/46, 116
See application file for complete search history.

(56) References Cited

U.S. PATENT DOCUMENTS

| 2,990,547 A | 6/1961 | McDougal |
| 3,662,758 A | 5/1972 | Glover |

(Continued)

FOREIGN PATENT DOCUMENTS

| CN | 1678370 | 10/2005 |
| CN | 101185789 | 5/2008 |

(Continued)

OTHER PUBLICATIONS

US 5,197,469 A, 03/1993, Adams (withdrawn)
(Continued)

Primary Examiner — Nicole F Lavert
(74) Attorney, Agent, or Firm — Fish & Richardson P.C.

(57) ABSTRACT

An implantable wireless lead includes an enclosure, the enclosure housing: one or more electrodes configured to apply one or more electrical pulses to a neural tissue; a first antenna configured to: receive, from a second antenna and through electrical radiative coupling, an input signal containing electrical energy, the second antenna being physically separate from the implantable neural stimulator lead; one or more circuits electrically connected to the first antenna, the circuits configured to: create the one or more electrical pulses suitable for stimulation of the neural tissue using the electrical energy contained in the input signal; and supply the one or more electrical pulses to the one or more electrodes, wherein the enclosure is shaped and arranged for delivery into a subject's body through an introducer or a needle.

20 Claims, 15 Drawing Sheets

Related U.S. Application Data continuation of application No. 14/972,386, filed on Dec. 17, 2015, now Pat. No. 9,789,314, which is a continuation of application No. 14/045,764, filed on Oct. 3, 2013, now Pat. No. 9,220,897, which is a continuation of application No. PCT/US2012/032200, filed on Apr. 4, 2012.

(60) Provisional application No. 61/471,496, filed on Apr. 4, 2011.

(51) Int. Cl.
 *A61N 1/372* (2006.01)
 *A61N 1/378* (2006.01)

(52) U.S. Cl.
 CPC ..... *A61N 1/37223* (2013.01); *A61N 1/37229* (2013.01); *A61N 1/36182* (2013.01)

(56) References Cited

U.S. PATENT DOCUMENTS

| | | |
|---|---|---|
| 3,663,758 A | 5/1972 | Erbert |
| 3,727,616 A | 4/1973 | Lenzkes |
| 4,057,069 A | 11/1977 | Dorffer et al. |
| 4,102,344 A | 7/1978 | Conway et al. |
| 4,223,679 A | 9/1980 | Schulman et al. |
| 4,494,950 A | 1/1985 | Fischell |
| 4,524,774 A | 6/1985 | Hildebrandt |
| 4,525,774 A | 6/1985 | Kino et al. |
| 4,532,930 A | 8/1985 | Crosby |
| 4,561,443 A | 12/1985 | Hogrefe et al. |
| 4,592,359 A | 6/1986 | Galbraith |
| 4,612,934 A | 9/1986 | Borkan |
| 4,628,933 A | 12/1986 | Michelson |
| 4,736,752 A | 4/1988 | Munck |
| 4,741,339 A | 5/1988 | Harrison et al. |
| 4,750,499 A | 6/1988 | Hoffer |
| 4,793,353 A | 12/1988 | Borkan |
| 4,837,049 A | 6/1989 | Byers et al. |
| 4,926,879 A | 5/1990 | Sevrain |
| 4,947,844 A | 8/1990 | McDermott |
| 5,058,581 A | 10/1991 | Silvian |
| 5,070,535 A | 12/1991 | Hochmair et al. |
| 5,193,539 A | 3/1993 | Schulman et al. |
| 5,262,793 A | 11/1993 | Sperry |
| 5,314,458 A | 5/1994 | Najafi et al. |
| 5,343,766 A | 9/1994 | Lee |
| 5,358,514 A | 10/1994 | Schulman et al. |
| 5,411,535 A | 5/1995 | Fujii et al. |
| 5,583,510 A | 12/1996 | Ponnapalli et al. |
| 5,591,217 A | 1/1997 | Barreras |
| 5,626,630 A | 5/1997 | Markowitz et al. |
| 5,735,887 A | 4/1998 | Barreras, Sr. et al. |
| 5,769,877 A | 6/1998 | Barreras |
| 5,861,019 A | 1/1999 | Sun et al. |
| 5,991,664 A | 11/1999 | Seligman |
| 5,995,874 A | 11/1999 | Borza |
| 6,141,588 A | 10/2000 | Cox et al. |
| 6,164,284 A | 12/2000 | Shulman et al. |
| 6,175,752 B1 | 1/2001 | Say et al. |
| 6,350,335 B1 | 2/2002 | Hampel et al. |
| 6,364,889 B1 | 4/2002 | Kheiri et al. |
| 6,415,184 B1 | 7/2002 | Ishikawa et al. |
| 6,445,953 B1 | 9/2002 | Bulkes et al. |
| 6,445,955 B1 | 9/2002 | Michelson et al. |
| 6,458,157 B1 | 10/2002 | Suaning |
| 6,463,336 B1 | 10/2002 | Mawhinney |
| D466,487 S | 12/2002 | Wada et al. |
| 6,516,227 B1 | 2/2003 | Meadows et al. |
| D474,982 S | 5/2003 | Wilson |
| 6,564,807 B1 | 5/2003 | Schulman et al. |
| 6,611,715 B1 | 8/2003 | Boveja |
| 6,615,081 B1 | 9/2003 | Boveja |
| 6,647,296 B2 | 11/2003 | Fischell et al. |
| 6,662,052 B1 | 12/2003 | Sarwal et al. |
| 6,684,104 B2 | 1/2004 | Gordon et al. |
| 6,690,974 B2 | 2/2004 | Archer et al. |
| 6,889,086 B2 | 5/2005 | Mass et al. |
| 6,895,280 B2 | 5/2005 | Meadows et al. |
| 6,972,727 B1 | 12/2005 | West et al. |
| 7,003,350 B2 | 2/2006 | Denker et al. |
| 7,027,874 B1 | 4/2006 | Sawan et al. |
| 7,110,823 B2 | 9/2006 | Whitehurst et al. |
| D529,402 S | 10/2006 | Burton |
| 7,177,690 B2 | 2/2007 | Woods et al. |
| 7,214,189 B2 | 5/2007 | Zdeblick |
| 7,277,728 B1 | 10/2007 | Kauhanen |
| 7,283,875 B2 | 10/2007 | Larsson |
| 7,317,947 B2 | 1/2008 | Wahlstrand et al. |
| 7,436,752 B2 | 10/2008 | He |
| 7,450,992 B1 | 11/2008 | Cameron |
| 7,471,257 B2 | 12/2008 | Candal et al. |
| 7,489,248 B2 | 2/2009 | Gengel et al. |
| 7,616,991 B2 | 11/2009 | Mann et al. |
| 7,620,451 B2 | 11/2009 | Demarais |
| 7,630,771 B2 | 12/2009 | Cauller |
| 7,664,552 B2 | 2/2010 | Wahlstrand et al. |
| D612,543 S | 3/2010 | Marseille |
| 7,729,781 B2 | 6/2010 | Swoyer et al. |
| 7,738,964 B2 | 6/2010 | Von Arx et al. |
| 7,741,734 B2 | 6/2010 | Joannopoulos et al. |
| 7,765,013 B2 | 7/2010 | Buick et al. |
| 7,853,333 B2 | 12/2010 | Demarais |
| 7,869,885 B2 | 1/2011 | Begnaud et al. |
| 7,894,905 B2 | 2/2011 | Pless et al. |
| 7,904,170 B2 | 3/2011 | Harding |
| 7,908,014 B2 | 3/2011 | Schulman et al. |
| 7,939,346 B2 | 5/2011 | Blick et al. |
| D658,302 S | 4/2012 | Nixon |
| 8,170,672 B2 | 5/2012 | Weiss et al. |
| 8,242,968 B2 | 8/2012 | Conrad et al. |
| 8,320,850 B1 | 11/2012 | Khlat |
| 8,332,040 B1 | 12/2012 | Winstrom |
| 8,634,928 B1 | 1/2014 | O'Drisco et al. |
| D701,504 S | 3/2014 | Christopher et al. |
| D703,204 S | 4/2014 | Riddiford et al. |
| D714,288 S | 9/2014 | Aumiller et al. |
| 8,849,412 B2 | 9/2014 | Perryman et al. |
| 8,903,502 B2 | 12/2014 | Perryman |
| D721,701 S | 1/2015 | Al-Nasser |
| D725,071 S | 3/2015 | Lee et al. |
| D725,072 S | 3/2015 | Kim et al. |
| D725,652 S | 3/2015 | Ishii |
| D734,330 S | 7/2015 | Huang et al. |
| 9,199,089 B2 | 12/2015 | Perryman et al. |
| 9,220,897 B2 | 12/2015 | Perryman et al. |
| 9,242,103 B2 | 1/2016 | Perryman et al. |
| 9,254,393 B2 | 2/2016 | Perryman et al. |
| 9,409,029 B2 | 8/2016 | Perryman et al. |
| 9,409,030 B2 | 8/2016 | Perryman et al. |
| 9,566,449 B2 | 2/2017 | Perryman et al. |
| 9,757,571 B2 | 9/2017 | Perryman |
| 9,789,314 B2 | 10/2017 | Perryman |
| 9,925,384 B2 | 3/2018 | Perryman et al. |
| 9,974,965 B2 | 5/2018 | Andresen et al. |
| 10,238,874 B2 | 3/2019 | Perryman |
| 10,258,800 B2 | 4/2019 | Perryman |
| 10,293,169 B2 | 5/2019 | Perryman et al. |
| 10,315,039 B2 | 6/2019 | Perryman et al. |
| 10,420,947 B2 | 9/2019 | Perryman et al. |
| 10,471,262 B2 | 11/2019 | Perryman et al. |
| 2001/0010662 A1 | 8/2001 | Saitou et al. |
| 2002/0095195 A1 | 7/2002 | Mass et al. |
| 2002/0123779 A1 | 9/2002 | Von Arx et al. |
| 2003/0078633 A1 | 4/2003 | Firlik et al. |
| 2003/0114898 A1 | 6/2003 | Von Arx et al. |
| 2003/0114899 A1 | 6/2003 | Woods et al. |
| 2003/0139782 A1 | 7/2003 | Duncan et al. |
| 2003/0169207 A1 | 9/2003 | Beigel |
| 2003/0204224 A1 | 10/2003 | Torgerson et al. |
| 2004/0044385 A1 | 3/2004 | Fenn et al. |
| 2004/0059392 A1 | 3/2004 | Parramon et al. |
| 2004/0082979 A1 | 4/2004 | Tong et al. |

(56) References Cited

U.S. PATENT DOCUMENTS

| | | |
|---|---|---|
| 2004/0127942 A1 | 7/2004 | Yomtov et al. |
| 2004/0138723 A1 | 7/2004 | Malick et al. |
| 2004/0167587 A1 | 8/2004 | Thompson et al. |
| 2004/0176803 A1 | 9/2004 | Whelan et al. |
| 2004/0220621 A1 | 11/2004 | Zhou |
| 2004/0230263 A1 | 11/2004 | Samulski |
| 2004/0243208 A1 | 12/2004 | Jordan |
| 2005/0119716 A1 | 6/2005 | McClure et al. |
| 2005/0137668 A1 | 6/2005 | Khan |
| 2005/0245994 A1 | 11/2005 | Varrichio et al. |
| 2006/0001583 A1 | 1/2006 | Bisig |
| 2006/0003721 A1 | 1/2006 | Bisig |
| 2006/0085039 A1 | 4/2006 | Hastings et al. |
| 2006/0085042 A1 | 4/2006 | Hastings et al. |
| 2006/0149331 A1 | 7/2006 | Man et al. |
| 2006/0161216 A1 | 7/2006 | Constance |
| 2006/0161225 A1 | 7/2006 | Sormann et al. |
| 2006/0178718 A1 | 8/2006 | Jordan |
| 2006/0287686 A1 | 12/2006 | Cullen et al. |
| 2006/0289528 A1 | 12/2006 | Chiu et al. |
| 2007/0055322 A1 | 3/2007 | Forsberg et al. |
| 2007/0055324 A1 | 3/2007 | Thompson et al. |
| 2007/0066995 A1 | 3/2007 | Strother et al. |
| 2007/0100385 A1 | 5/2007 | Rawat et al. |
| 2007/0100395 A1 | 5/2007 | Ibrahim |
| 2007/0100935 A1 | 5/2007 | Miyazaki et al. |
| 2007/0106337 A1 | 5/2007 | Errico et al. |
| 2007/0109208 A1 | 5/2007 | Turner |
| 2007/0112402 A1 | 5/2007 | Grill et al. |
| 2007/0156179 A1 | 7/2007 | S.E. |
| 2007/0208394 A1 | 9/2007 | King et al. |
| 2007/0213773 A1 | 9/2007 | Hill et al. |
| 2007/0213783 A1 | 9/2007 | Pless |
| 2007/0254632 A1 | 11/2007 | Beadle et al. |
| 2007/0255373 A1 | 11/2007 | Metzler et al. |
| 2007/0265543 A1 | 11/2007 | VanSickle et al. |
| 2007/0265690 A1 | 11/2007 | Lichtenstein et al. |
| 2007/0288066 A1 | 12/2007 | Christman et al. |
| 2008/0010358 A1 | 1/2008 | Jin |
| 2008/0046012 A1 | 2/2008 | Covalin et al. |
| 2008/0077184 A1 | 3/2008 | Denker et al. |
| 2008/0077188 A1 | 3/2008 | Denker et al. |
| 2008/0077189 A1 | 3/2008 | Ostroff |
| 2008/0103558 A1 | 5/2008 | Wenzel |
| 2008/0154217 A1 | 6/2008 | Carrez et al. |
| 2008/0266123 A1 | 10/2008 | Ales et al. |
| 2008/0281244 A1 | 11/2008 | Jacobs |
| 2009/0018599 A1 | 1/2009 | Hastings et al. |
| 2009/0099405 A1 | 4/2009 | Schneider et al. |
| 2009/0105784 A1 | 4/2009 | Massoud-Ansari |
| 2009/0125091 A1 | 5/2009 | Schoenbach et al. |
| 2009/0132002 A1 | 5/2009 | Kieval |
| 2009/0132003 A1 | 5/2009 | Borgens et al. |
| 2009/0200985 A1 | 8/2009 | Zane et al. |
| 2009/0204170 A1 | 8/2009 | Hastings et al. |
| 2009/0234407 A1 | 9/2009 | Hastings et al. |
| 2009/0248112 A1 | 10/2009 | Mumbru et al. |
| 2009/0292339 A1 | 11/2009 | Erickson |
| 2010/0053789 A1 | 3/2010 | Duric et al. |
| 2010/0114198 A1 | 5/2010 | Donofrio et al. |
| 2010/0125269 A1* | 5/2010 | Emmons ............ A61B 18/18 606/33 |
| 2010/0137938 A1 | 6/2010 | Kishawi et al. |
| 2010/0168818 A1 | 7/2010 | Barror et al. |
| 2010/0174340 A1 | 7/2010 | Simon |
| 2010/0179449 A1 | 7/2010 | Chow et al. |
| 2010/0198039 A1 | 8/2010 | Towe |
| 2010/0198307 A1 | 8/2010 | Toy et al. |
| 2010/0231382 A1 | 9/2010 | Tayrani et al. |
| 2010/0234922 A1 | 9/2010 | Forsell |
| 2010/0241051 A1 | 9/2010 | Dacey, Jr. et al. |
| 2010/0268298 A1 | 10/2010 | Moffitt et al. |
| 2010/0269339 A1 | 10/2010 | Dye et al. |
| 2010/0298742 A1 | 11/2010 | Perlman et al. |
| 2010/0331934 A1 | 12/2010 | McDonald et al. |
| 2011/0029043 A1 | 2/2011 | Frysz et al. |
| 2011/0040350 A1 | 2/2011 | Griffith |
| 2011/0054563 A1 | 3/2011 | Janzig et al. |
| 2011/0074342 A1 | 3/2011 | MacLaughlin |
| 2011/0077698 A1 | 3/2011 | Tsampazis et al. |
| 2011/0098583 A1 | 4/2011 | Pandia et al. |
| 2011/0106220 A1 | 5/2011 | DeGiorgio et al. |
| 2011/0120822 A1 | 5/2011 | Kondou et al. |
| 2011/0121822 A1 | 5/2011 | Parsche |
| 2011/0125214 A1 | 5/2011 | Goetz et al. |
| 2011/0130804 A1 | 6/2011 | Lin et al. |
| 2011/0144468 A1 | 6/2011 | Boggs et al. |
| 2011/0152750 A1 | 6/2011 | Dacey et al. |
| 2011/0172733 A1 | 7/2011 | Lima et al. |
| 2011/0190849 A1 | 8/2011 | Faltys et al. |
| 2011/0245892 A1 | 10/2011 | Kast et al. |
| 2012/0004708 A1 | 1/2012 | Chen et al. |
| 2012/0004709 A1 | 1/2012 | Chen et al. |
| 2012/0143282 A1 | 6/2012 | Fukui et al. |
| 2012/0158407 A1 | 6/2012 | Forsell |
| 2012/0194399 A1 | 8/2012 | Bily et al. |
| 2012/0215218 A1 | 8/2012 | Lipani |
| 2012/0283800 A1 | 11/2012 | Perryman et al. |
| 2012/0330384 A1 | 12/2012 | Perryman et al. |
| 2013/0016016 A1 | 1/2013 | Lin et al. |
| 2013/0018439 A1 | 1/2013 | Chow et al. |
| 2013/0066400 A1 | 3/2013 | Perryman et al. |
| 2013/0079849 A1 | 3/2013 | Perryman et al. |
| 2013/0131752 A1 | 5/2013 | Rawat et al. |
| 2013/0165991 A1 | 6/2013 | Kim et al. |
| 2013/0310901 A1 | 11/2013 | Penyman et al. |
| 2014/0031837 A1 | 1/2014 | Perryman et al. |
| 2014/0047713 A1 | 2/2014 | Singh et al. |
| 2014/0058480 A1 | 2/2014 | Perryman et al. |
| 2014/0058481 A1 | 2/2014 | Perryman et al. |
| 2014/0169142 A1 | 6/2014 | Heck et al. |
| 2014/0266935 A1 | 9/2014 | Tankiewicz |
| 2014/0336727 A1 | 11/2014 | Penyman et al. |
| 2015/0182753 A1 | 7/2015 | Harris et al. |
| 2015/0321017 A1 | 11/2015 | Penyman et al. |
| 2016/0101287 A1 | 4/2016 | Perryman et al. |
| 2016/0136438 A1 | 5/2016 | Perryman et al. |
| 2016/0136439 A1 | 5/2016 | Perryman et al. |
| 2016/0339258 A1 | 11/2016 | Penyman et al. |
| 2016/0361535 A1 | 12/2016 | Perryman et al. |
| 2016/0367825 A1 | 12/2016 | Perryman et al. |
| 2017/0036033 A9 | 2/2017 | Perryman et al. |
| 2018/0008828 A1 | 1/2018 | Perryman et al. |
| 2018/0169423 A1 | 6/2018 | Perryman et al. |
| 2018/0236248 A1 | 8/2018 | Perryman et al. |
| 2018/0264277 A1 | 9/2018 | Perryman et al. |
| 2019/0217106 A1 | 7/2019 | Perryman et al. |
| 2019/0381327 A1 | 12/2019 | Perryman et al. |
| 2020/0016415 A1 | 1/2020 | Perryman et al. |
| 2020/0016416 A1 | 1/2020 | Perryman et al. |
| 2020/0222703 A1 | 7/2020 | Perryman et al. |

FOREIGN PATENT DOCUMENTS

| | | |
|---|---|---|
| CN | 101217320 | 7/2008 |
| CN | 101352596 | 1/2009 |
| CN | 101773701 | 7/2010 |
| CN | 101842131 | 9/2010 |
| CN | 201676401 | 12/2010 |
| CN | 102120060 | 7/2011 |
| EP | 2462981 | 6/2001 |
| EP | 1588609 | 10/2005 |
| EP | 2694154 | 1/2018 |
| ES | 2341347 | 6/2010 |
| JP | H0509901 | 9/1998 |
| JP | 2002524124 | 8/2002 |
| JP | 2005531371 | 10/2005 |
| JP | 200823353 | 2/2008 |
| JP | 2008161667 | 7/2008 |
| JP | 2008528222 | 7/2008 |
| JP | 2009523402 | 6/2009 |
| JP | 2010534114 | 11/2010 |
| JP | 201155912 | 3/2011 |
| JP | 2011510787 | 4/2011 |

(56) References Cited

FOREIGN PATENT DOCUMENTS

| WO | WO9620754 | 7/1996 |
|---|---|---|
| WO | WO 200013585 | 3/2000 |
| WO | WO2004002572 | 1/2004 |
| WO | WO 2004004826 | 1/2004 |
| WO | WO 2006113802 | 10/2006 |
| WO | WO 2007059386 | 5/2007 |
| WO | WO 2007081971 | 7/2007 |
| WO | WO2009015005 | 1/2009 |
| WO | WO 2010051189 | 5/2010 |
| WO | WO 2010053789 | 5/2010 |
| WO | WO 2010057046 | 5/2010 |
| WO | WO 2010104569 | 9/2010 |
| WO | WO 2011079309 | 6/2011 |
| WO | WO 2012103519 | 8/2012 |
| WO | WO 2012138782 | 10/2012 |
| WO | WO 2013019757 | 2/2013 |
| WO | WO 2013025632 | 2/2013 |
| WO | WO 2013040549 | 3/2013 |

OTHER PUBLICATIONS

PCT International Search Report and Written Opinion in International Appln. No. PCT/US2020/013155, dated Apr. 1, 2020, 8 pages.
European Search Report in European Appln. No. EP19186209, dated Nov. 25, 2019, 9 pages.
U.S. Appl. No. 14/445,159, filed Nov. 13, 2014, Perryman et al.
U.S. Appl. No. 29/478,687, filed Jan. 7, 2003, Perryman et al.
Associate letter reporting Office Action in Application No. MX/a/2013/008690, dated Feb. 12, 2016, 1 page.
AU Office Action issued in Australian Appln. No. 2015259305, dated Feb. 13, 2019, 3 pages.
Chinese Office Action in Chinese Appln. No. 201280006578.7, dated Dec. 8, 2014.
Chinese Office Action in Chinese Appln. No. 201280006578.7, dated Jul. 29, 2014, 6 pages.
Chinese Office action in Chinese Appln. No. 201280006578.7, dated Mar. 2, 2016, 5 pages.
Chinese Office Action in Chinese Appln. No. 201280017245, dated Mar. 2, 2016, 6 pages.
Chinese Office Action in Chinese Appln. No. 201280017245.4, dated Aug. 3, 2015, 16 pages (with English translation).
Chinese Office Action in Chinese Appln. No. 201280017245.4, dated Dec. 3, 2014, 6 pages (with English translation).
Chinese Office Action in Chinese Appln. No. 201280037814, dated May 6, 2015, 18 pages (with English translation).
Chinese Office Action in Chinese Appln. No. 201280037814.1 dated Mar. 7, 2016, 13 pages.
Chinese Office Action in Chinese Appln. No. 201611007072.4, dated Jun. 4, 2019, 9 pages.
CN Office Action in Chinese Appln No. 201580036252.2, dated Sep. 30, 2018, 87 pages.
Communication from the European Patent Office in EP Appln. No. 12767575.9, dated Nov. 7, 2014, 7 pages.
EP European Search Report in European Appln. No. 17208566.4, dated Sep. 26, 2018, 14 pages.
EP Office Action in European Appln. No. 12740011.7, dated Sep. 18, 2018, 21 pages.
EP Office Action in European Appln. No. 15793285.6, dated Oct. 4, 2018, 6 pages.
EP Partial Supplementary European Search Report in European Appln. No. 12831083.6, dated Mar. 24, 2015, 7 pages.
European Search Report in European Appln. No. 12767575.9, dated Jan. 11, 2018, 6 pages.
Examination Report in Appln. No. 2012240239, dated May 9, 2016, 3 pages.
Examination Report in Appln. No. 2012308197, dated Apr. 22, 2016, 5 pages.
Extended European Search report in Appln. No. 12740011.7, dated Sep. 9, 2015, 6 pages.
Extended European Search report in Appln. No. 12767575.9, dated Nov. 7, 2014, 7 pages.
Extended European Search Report in Appln. No. 1281083.6, dated Aug. 17, 2015, 9 pages.
Extended European Search report in Appln. No. 12819482.6, dated Apr. 28, 2015, 7 pages.
Extended European Search Report in Appln. No. 12824347.4, dated Apr. 22, 2015, 6 pages.
Extended European Search Report in Appln. No. 12824347.4, dated May 11, 2015, 1 page.
Extended European Search Report in Appln. No. 15793285.6, dated Dec. 12, 2017, 7 pages.
EP Extended European Search Report in European Appln. No. 18150779.9, dated May 9, 2018, 7 pages.
Iannetta [online], "Nov. 2014 New Products: Wearable coil facilities positioning during prostate MRI," Urology Times, retrieved on Nov. 10, 2014, retrieved from<URL: http://urologytimes.modernmedicine.com/urology-times/news/november-2014-new-products-wearable-coil-facilitates-positioning-during-prostate-mri?page=full>, 7 pages.
Israel Office Action in Israel Appln. No. 228485, dated Jan. 16, 2017, 16 pages.
Japanese Office Action in Japanese Appln. No. 2013-551396, dated Jan. 12, 2016, 7 pages (with English translations).
Japanese Office Action in Japanese Appln. No. 2014-503961, dated Mar. 30, 2016, 10 pages.
Japanese Office Action in Japanese Appln. No. 2014-503961, dated Nov. 8, 2017 (with English Translation).
Japanese Office Action in Japanese Appln. No. 2018-042014, dated Apr. 15, 2019, 8 pages.
O'Driscoll et al., "A mm-Sized implantable power receiver with adaptive link compensation," Poster, Presented at IEEE International Soild-State Corcuits Conference, Session 17, 2009, 3 pages.
PCT International Preliminary Report on Patentability and Written Opinion in International Appln. No. PCT/US2012/023029, dated Jan. 28, 2014, 9 pages.
PCT International Preliminary Report on Patentability and Written Opinion in International Appln. No. PCT/US2012/032200 dated Oct. 8, 2013, 11 pages.
PCT International Preliminary Report on Patentability and Written Opinion in International Appln. No. PCT/US2012/048903, dated Mar. 25, 2014, 8 pages.
PCT International Preliminary Report on Patentability in International Appln. No. PCT/US2013/077846, dated Jun. 30, 2015, 6 pages.
PCT International Preliminary Report on Patentability in International Appln. No. PCT/US2015/030433, dated Nov. 15, 2016, 10 pages.
PCT International Preliminary Report on Patentability issued in International Appl. No. PCT/US2012/055746, dated Mar. 18, 2014, 10 pages.
PCT International Preliminary Report on Patentability issued in International Appln. No. PCT/US2012/050633, dated Feb. 18, 2014, 7 pages.
PCT International Search Report and PCT Written Opinion of the International Searching Authority in International Appln. No. PCT/US2012/55746, dated Jan. 3, 2013, 11 pages.
PCT International Search Report and the Written Opinion in Appln. No. PCT/US2012/048903 dated Oct. 10, 2012, 10 pages.
PCT International Search Report and Written Opinion in International Appln. No. IPCT/US12/50633 dated Oct. 23, 2012, 8 pages.
PCT International Search Report and Written Opinion in International Appln. No. PCT/US2012/023029, dated May 16, 2012, 11 pages.
PCT International Search Report and Written Opinion in International Appln. No. PCT/US2012/032200, dated Jul. 27, 2012, 11 pages.
PCT International Search Report and Written Opinion in International Appln. No. PCT/US2013/077846 dated Apr. 21, 2014, 10 pages.
PCT International Search Report and Written Opinion in International Appln. No. PCT/US2015/030433, dated Sep. 29, 2015, 14 pages.

(56) References Cited

OTHER PUBLICATIONS pharad.com [online], "Assembly, Wearable Antenna, 350-450 MHz," retrieved on Oct. 14, 2010, retrieved from URL< http://www.pharad.com/pdf/UHF-Wearable-Antenna-2D.pdf>, 1 page.
Poon et al., "Optimal frequency for wireless power transmission into dispersive tissue," IEEE Transactions on Antennas and Propagation, May 2010, 58(5):1739-1750.
U.S. Non-Final Office Action for U.S. Appl. No. 13/584,618, dated May 23, 2013, 6 pages.
U.S. Notice of Allowance for U.S. Appl. No. 14/068,750, dated Jun. 13, 2016, 5 pages.
U.S. Advisory Action for U.S. Appl. No. 13/551,050, dated Apr. 24, 2015, 3 pages.
U.S. Advisory Action for U.S. Appl. No. 13/621,530, dated May 11, 2015, 3 pages.
U.S. Final Office Action for U.S. Appl. No. 13/551,050, dated Feb. 13, 2015, 18 pages.
U.S. Final Office Action for U.S. Appl. No. 13/562,221, dated Oct. 23, 2014, 22 pages.
U.S. Final Office Action for U.S. Appl. No. 13/584,618, dated Aug. 26, 2013, 13 pages.
U.S. Final Office Action for U.S. Appl. No. 13/621,530, dated Jan. 5, 2015, 32 pages.
U.S. Final Office Action for U.S. Appl. No. 14/068,750 dated Jul. 29, 2015, 18 pages.
U.S. Final Office Action for U.S. Appl. No. 14/141,197, dated Jul. 8, 2015, 11 pages.
U.S. Final Office Action for U.S. Appl. No. 14/445,159, dated Jun. 9, 2016, 9 pages.
U.S. Final Office Action in U.S. Appl. No. 14/445,159, dated Dec. 15, 2015, 7 pages.
U.S. Non-Final Office Action for U.S. Appl. No. 14/045,764 dated Apr. 1, 2015, 15 pages.
U.S. Non-Final Office Action for U.S. Appl. No. 14/045,764 dated Feb. 6, 2015, 14 pages.
U.S. Non-Final Office Action for U.S. Appl. No. 13/551,050 dated Mar. 4, 2014, 30 pages.
U.S. Non-Final Office Action for U.S. Appl. No. 13/551,050 dated Sep. 24, 2015, 16 pages.
U.S. Non-Final Office Action for U.S. Appl. No. 13/562,221, dated Jan. 29, 2014, 30 pages.
U.S. Non-Final Office Action for U.S. Appl. No. 13/584,618 dated Jun. 12, 2013, 15 pages.
U.S. Non-Final Office Action for U.S. Appl. No. 13/621,530, dated Apr. 11, 2014, 15 pages.
U.S. Non-final Office Action for U.S. Appl. No. 13/897,427, dated Jan. 9, 2014, 24 pages.
U.S. Non-Final Office Action for U.S. Appl. No. 14/068,750 dated Jan. 9, 2015, 27 pages.
U.S. Non-Final Office Action for U.S. Appl. No. 14/141,197, dated Mar. 4, 2015, 11 pages.
U.S. Non-Final Office Action for U.S. Appl. No. 14/710,548, dated Dec. 18, 2015, 6 pages.
U.S. Non-Final Office Action for U.S. Appl. No. 29/478,687, dated Aug. 12, 2015, 8 pages.
U.S. Non-final Office Action in U.S. Appl. No. 14/068,750, dated Jan. 4, 2016, 13 pages.
U.S. Notice of Allowance for U.S. Appl. No. 13/551,050 dated Apr. 6, 2016, 7 pages.
U.S. Notice of Allowance for U.S. Appl. No. 13/562,221, dated Jul. 21, 2015, 8 pages.
U.S. Notice of Allowance for U.S. Appl. No. 13/584,618, dated May 16, 2014, 8 pages.
U.S. Notice of Allowance for U.S. Appl. No. 13/621,530, dated Aug. 20, 2015, 9 pages.
U.S. Notice of Allowance for U.S. Appl. No. 13/621,530, dated Oct. 7, 2015, 4 pages.
U.S. Notice of Allowance for U.S. Appl. No. 13/897,427, dated Jul. 28, 2014, 8 pages.
U.S. Notice of Allowance for U.S. Appl. No. 13/897,427, dated Sep. 24, 2014, 4 pages.
U.S. Notice of Allowance for U.S. Appl. No. 14/045,764, dated Aug. 17, 2015, 11 pages.
U.S. Notice of Allowance for U.S. Appl. No. 14/710,548, dated Apr. 4, 2016, 6 pages.
U.S. Office Action for U.S. Appl. No. 13/551,050 dated Sep. 12, 2013, 8 pages.
U.S. Office Action for U.S. Appl. No. 13/562,221, dated Sep. 13, 2013, 7 pages.
U.S. Notice of Allowance for U.S. Appl. No. 14/141,197, dated Sep. 30, 2015, 7 pages.
U.S. Advisory Action for U.S. Appl. No. 13/584,618, dated Nov. 1, 2013, 3 pages.
wirelessdesignmag.com [online], "Pharad at Forefront of LTE Antenna Innovation with Development of LTE Wearable Antenna," retrieved on Aug. 12, 2012, retrieved from<URL:http://www.wirelessdesignmag.com/product-release/2013/08/pharad-forefront-lte-antenna-innovation-development-lte-wearable-antenna>, 3 pages.
IL Office Action in Israeli Appln. No. 256280.0, dated Sep. 16, 2020, 9 pages (with English Translation).
CN OA in Chinese Appln. No. 201710675346.5, dated Jun. 1, 2020, 11 pages (with English translation).
CA Office Action in Canadian Appln. No. 2831138, dated Oct. 30, 2020, 4 pages.

\* cited by examiner

IMPLANTABLE LEAD

CROSS-REFERENCE TO RELATED APPLICATIONS

This application is a continuation of U.S. patent application Ser. No. 14/709,962, filed Sep. 20, 2017, now allowed, which is a continuation of U.S. application Ser. No. 14/972,386, filed on Dec. 17, 2015, now U.S. Pat. No. 9,789,314, issued Oct. 17, 2017, which is a continuation of U.S. application Ser. No. 14/045,764, filed on Oct. 3, 2013, now U.S. Pat. No. 9,220,897, issued on Dec. 29, 2015, which is a continuation of PCT Application No. PCT/US2012/032200, international filing date Apr. 4, 2012, which claims the benefit of U.S. Provisional Patent Application 61/471,496, filed Apr. 4, 2011. All prior applications are hereby incorporated by reference in their entirety.

TECHNICAL FIELD

This description is related to implantable neural stimulators.

BACKGROUND

A variety of therapeutic intra-body electrical stimulation techniques can treat neuropathic conditions. These techniques may utilize a subcutaneous battery operated implantable pulse generator (IPG) connected to one or more implantable wired leads. These leads have numerous failure modes, including mechanical dislodgement, impingement of the lead-extension tubing, infection, and uncomfortable irritation from the IPG and extension tubing. Various types of spinal cord stimulation (SCS) leads have been used to provide therapeutic pain relief. These lead configurations often include cylindrical percutaneous leads and paddle lead form factors. Cylindrical percutaneous leads typically have diameters in the range of 1.3 mm and contain a number of circular electrodes used for effectiveness testing during a trial implant period, and in many cases for the permanent implantation. Paddle leads, however, contain electrodes with a greater surface area directionally targeted for control over the excitation of the nerve bundles and may require surgical laminotomy.

SUMMARY

Some embodiments provide an implantable neural stimulator wireless lead. The wireless lead includes: an enclosure; the enclosure housing; a) one or more electrodes configured to apply one or more electrical pulses to a neural tissue; b) a first antenna configured to receive, from a second antenna through electrical radiative coupling, an input signal containing electrical energy, the second antenna being physically separate from the implantable neural stimulator lead; c) one or more circuits electrically connected to the first antenna, the circuits configured to create the one or more electrical pulses suitable for stimulation of the neural tissue using the electrical energy contained in the input signal, and supply the one or more electrical pulses to the one or more electrodes, wherein the enclosure is shaped and arranged for delivery into a subject's body through an introducer or a needle.

Embodiments may include one or more features. For example, a portion of the enclosure may leave the electrodes in a non-direct contact with the neural tissue after the lead has been delivered into the subject's body. The enclosure can be semi-cylindrical in shape and the electrodes may include at least one directional electrode that directs a current path associated with the one or more electrical pulses to a direction that is substantially perpendicular to the neural tissue. The electrodes may include a semi-cylindrical array of electrodes. The electrodes may be made of at least one of: platinum, platinum-iridium, gallium-nitride, titanium-nitride, iridium-oxide, or combinations thereof. The electrodes can include two to sixteen electrodes, each having a longitudinal length between 1.0 and 6.0 mm and a width between 0.4 and 3.0 mm. The electrodes are spaced between 1 mm to 6 mm apart and have a combined surface area of between 0.8 $mm^2$ to 60.00 $mm^2$.

The lead may be a paddle-style lead. Specifically, the lead can be a paddle lead with a height between 1.3 mm and 2.0 mm, and a width between 2.0 mm and 4.0 mm. The lead can be shaped concavely to secure a lateral position on the neural tissue after the lead has been delivered into the subject's body. The lateral position may be with regard to a dorsal aspect of the subject's spinal cord. For example, the lead has a concave profile between 1.0 mm and 1.5 mm, and a concave edge between 0.2 mm and 0.3 mm.

The lead can be delivered into an epidual space of a subject's body. The delivery can be through a needle, such as, for example, a tuohy needle, no larger than gauge 14. The lead may be delivered to treat a neural tissue associated with the spinal column.

The enclosure can further house a lumen to operate a navigating stylet during delivery of the enclosure. The enclosure may further include a distal tip. The distal tip can be rounded with a length of between 0.5 mm and 2.0 mm. The distal tip can also be pointed with a length of between 2.0 and 6.0 mm. The enclosure may have an external coating of bio-compatible polymer, the polymer includes at least one of: polymethymethacrylate (PMMA), polydimethylsiloxane (PDMS), parylene, polyurethance, polytetrafluoroethylene (PTFE), or polycarbonate. The enclosure may further have an external coating of silicone elastomer. The enclosure can further house antenna coupling contacts, the antenna contacts being electrically connected to the antennas and the circuit and configured to couple the antenna with the surrounding tissue. The antenna coupling contacts can include two to eight antenna-coupling pairs. The antenna coupling contacts may be located proximal, relative to the electrodes, in the enclosure. The antenna coupling contacts can each have a longitudinal length of between 1.0 mm and 6.0 mm, and a width of between 1.0 mm to 2.5 mm. The antenna coupling contacts can be spaced between 30 mm and 80 mm apart. At least one of the antennas can be constructed as a conductive trace contained on one of the circuits. At least one of the antennas can be fabricated as a conductive wire connected to one of the circuits. The circuits can be flexible circuits. The flexible circuits are capable of undergoing a bend radius of under 0.5 mm. The flexible circuits can be placed proximal, relative to the electrodes, in the enclosure. The flexible circuits can include a waveform conditioning circuit.

Some embodiments provide a method of treating neurological pain. The method includes: providing an implantable neural stimulator lead including an enclosure that houses: one or more electrodes; a first antenna configured to receive, from a second antenna and through electrical radiative coupling, an input signal containing electrical energy, the second antenna being physically separate from the implantable neural stimulator lead; one or more flexible circuits electrically connected to the first antenna, the flexible circuits configured to: create the one or more electrical pulses suitable to be applied at the electrodes using the electrical energy contained in the input signal; and supply the one or more electrical pulses to the one or more electrodes, and implanting the neural stimulator lead into a subject's body through an introducer or a needle.

Embodiments may include one or more of the following features. For example, a portion of the enclosure may leave the electrodes in a non-direct contact with a neural tissue after the lead has been implanted into the subject's body. The electrodes can include at least one directional electrode that confines a current path associated with the one or more electrical pulses in a direction substantially perpendicular to the neural tissue. The needle can be a tuohy needle no larger than gauge 14.

DETAILED DESCRIPTION

Figure 1:
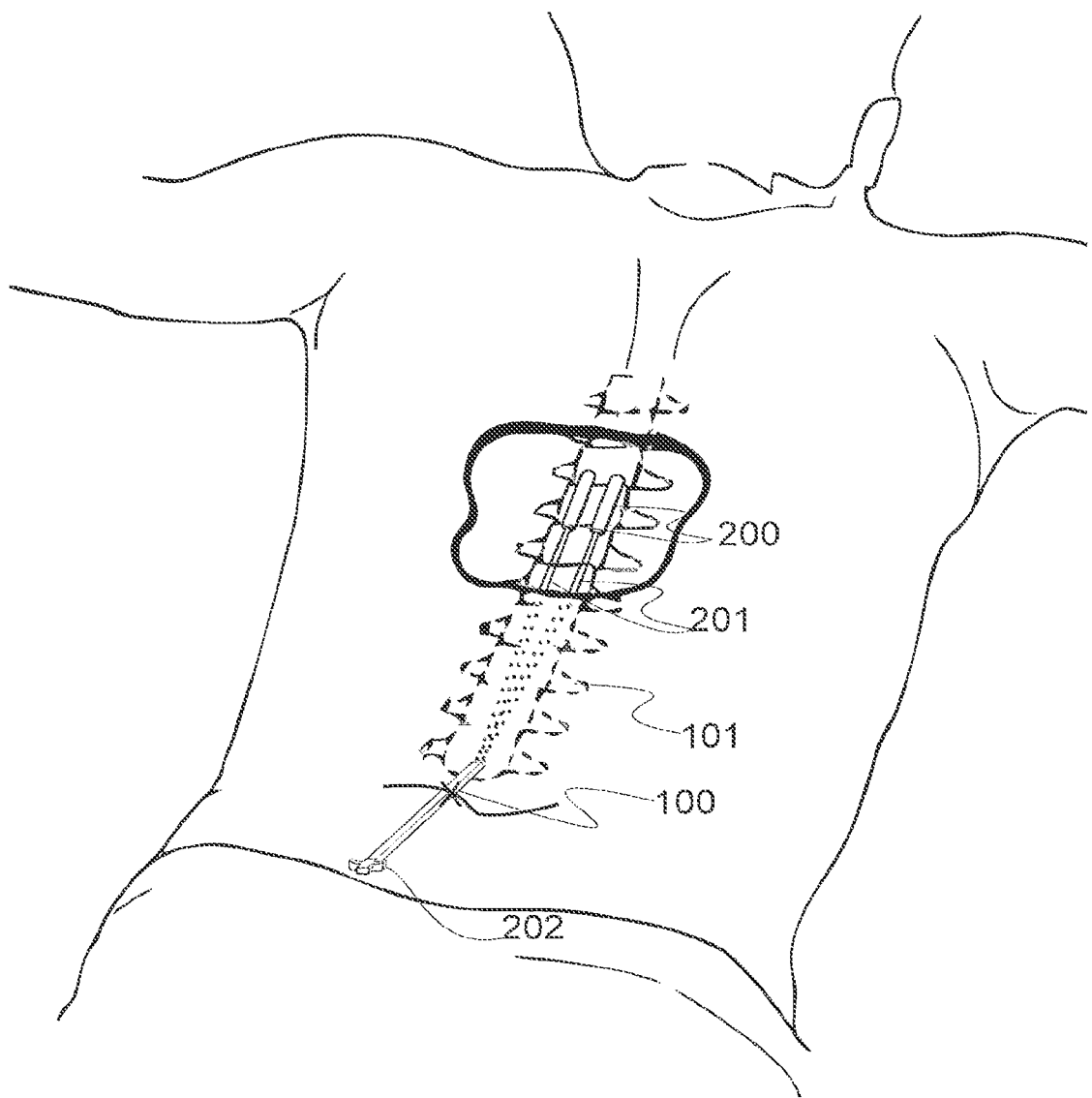
FIG. 1 illustrates two wireless paddle leads being implanted through an introducer into the epidural space.

Spinal cord stimulation may treat chronic neuropathic pain, especially low back pain and radiculopathy, vascular insufficiency in the feet or hands, angina, and more. In various implementations, a neural stimulation system can send electrical stimulation to targeted nerve tissue with neither cables nor inductive coupling to power the passive implanted stimulator. This can be used to treat pain or a variety of other modalities. The targeted nerve tissues may be, for example, in the spinal column including the spinothalamic tracts, dorsal horn, dorsal root ganglia, dorsal roots, dorsal column fibers, and peripheral nerves bundles leaving the dorsal column or brainstem, as well as any cranial nerves, abdominal, thoracic, or trigeminal ganglia nerves, nerve bundles of the cerebral cortex, deep brain and any sensory or motor nerves.

The neural simulation system can include an implantable lead that includes an enclosure that houses one or more conductive antennas (for example, dipole or patch antennas), internal circuitry for frequency waveform and electrical energy rectification, and one or more electrode pads allowing for neural stimulation of tissue. The neural stimulation system may receive microwave energy from an external source. The implantable lead may be 1.3 mm diameter or smaller. Particular implementations of the circuitry, antennas and pads are described in PCT Application PCT/US2012/023029, now expired while the US counterpart published as US-2012-0283800-A1 and issued as U.S. Pat. No. 9,409,030, which is incorporated herein by reference.

In various embodiments, the implantable lead is powered wirelessly (and therefore does not require a wired connection) and contains the circuitry necessary to receive the pulse instructions from a source external to the body. For example, various embodiments employ internal dipole (or other) antenna configuration(s) to receive RF power through electrical radiative coupling. This can allow such leads to produce electrical currents capable of stimulating nerve bundles without a physical connection to an implantable pulse generator (IPG) or use of an inductive coil. This can be advantageous relative to designs that employ inductive coils to receive RF power through inductive coupling and then transfer the received power to a large IPG device for recharging, particularly since the the large IPG device for recharging can be as large as 100 mm by 70 mm.

Furthermore, the electrical radiative coupling mechanism (for example, a dipole antenna) can be utilized to improve the form factor of a wireless lead and allow for miniature diameters, as small as 30 microns. For example, some implementations of the wireless lead, such as those discussed in association with FIGS. 7-15, can have diameters of less than 1.3 mm, and as small as 500 microns while still providing the same functionality as wired spinal cord stimulation leads.

Electrical radiative coupling also allows for the transmission and reception of energy at greater depths with less degradation in efficiency than inductive coil techniques. This can provide an advantage over devices that employ inductive coupling since the efficiency of such implants is highly dependent on the distance separating the external transmitter coil and the implanted receiver coil.

Various embodiments can also include distinct advantages over wired leads in regards to ease of insertion, cross connections, elimination of extension wires, and no requirement for an implantable pulse generator in order to administer a chronic therapy.

Various implementations also may have an associated lower overall cost compared to existing implantable neural modulation systems due to the elimination of the implantable pulse generator, and this may lead to wider adoption of neural modulation therapy for patients as well as reduction in overall cost to the healthcare system.

FIG. 1 illustrates two wireless paddle leads 200 (described in more detail below) being implanted through an extended-width introducer 202 into the epidural space. A lead 200 may be advanced and guided into the epidural space utilizing the extension tubing 201 with a handle for manipulating the lead 200. The introducer 202 has an entry point 100 above lumbar spinal column 103 (shown in FIG. 2). Once the introducer 202 is removed, the wireless paddle lead 200 can be anchored in place subcutaneously at entry point 100. Thereafter, extension tubing 201 may remain implanted and may run from the skin placement to the wireless paddle leads 200.

In some embodiments, the tubing 201 contains a lumen for a stylet (otherwise referred to as an "injector lead wire," a "guide-wire," a "navigation wire," or "a steer wire"), which can be used for placing the lead 200. The stylet may be made of metal and can provide steerability strength during implantation of the wireless paddle lead 200. After the wireless paddle lead 200 has been successfully deployed, the metal stylet may be removed. As will be discussed in association with FIG. 7C, this lumen, or other lumens in tubing 201, can be used to also house electronic circuitry.

Figure 2:
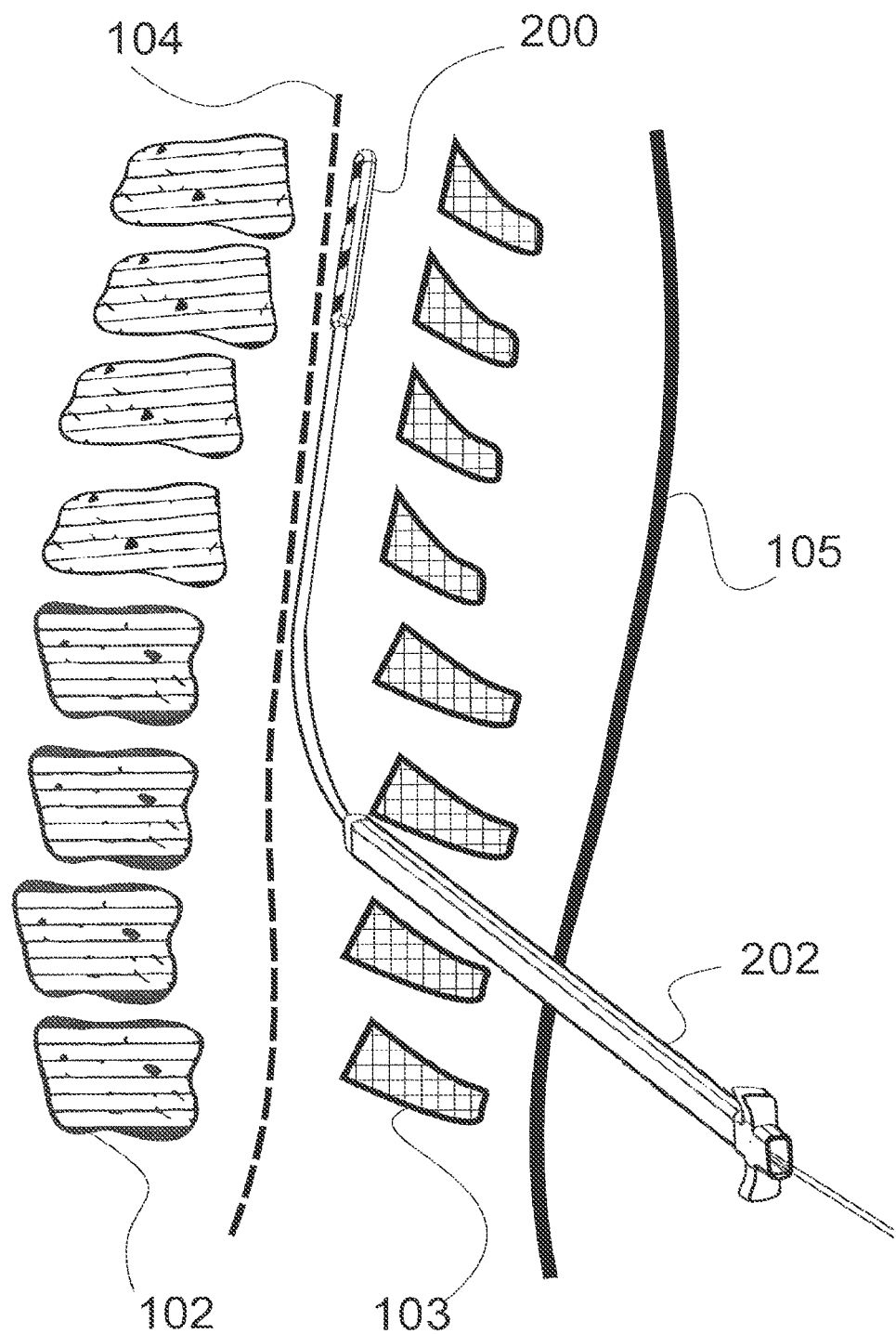
FIG. 2 illustrates a wireless paddle lead being implanted through an introducer into a human body.

FIG. 2 illustrates a wireless paddle lead 200 being placed through an introducer 202 typically in the lumbar region in between the L1 and L2 vertebrae. For example, the introducer 202 may be inserted through a small incision in the skin 105 and in between the vertebrae 103. In certain other embodiments, multiple wireless paddle leads 200, wireless cylindrical leads 400 (as will be discussed in association with FIGS. 8-15) and wireless semi-cylindrical leads 300 (as will be discussed in association with FIGS. 8-15) can be inserted through the same channel of introducer 202. Wireless paddle leads 200, cylindrical leads 400 or semi-cylindrical leads 300 for spinal cord stimulation applications can then be implanted and placed against the dura 104 of the spinal column 102, as described in association with FIG. 3 below.

In certain embodiments, wireless paddle leads 200, cylindrical leads 400 or semi-cylindrical leads 300 may be adapted to be located within the epidural space of the spinal column, near or on the dura of the spinal column, in tissue in close proximity to the spinal column, in tissue located near the dorsal horn, dorsal root ganglia, dorsal roots, dorsal column fibers and/or peripheral nerve bundles leaving the dorsal column of the spine.

In certain embodiments, wireless paddle leads 200, cylindrical leads 400 or semi-cylindrical leads 300 can be adapted to be placed and secured to stimulate nerves leaving the spinal column for the treatment of a variety of conditions, such as, for example, pain, angina, peripheral vascular disease, gastrointestinal disorders. In other embodiments, wireless paddle leads 200 can be adapted to treat other conditions via neural stimulation of nerve bundles emanating from the spine. "Spinal cord tissue" and "nerve bundles emanating from the spine" generally refer to, without limitation, the nerve bundles ranging from spinal column levels C1 to L5, dorsal horn, dorsal root ganglia, dorsal roots, dorsal column fibers and peripheral nerve bundles leaving the dorsal column.

Figure 3:
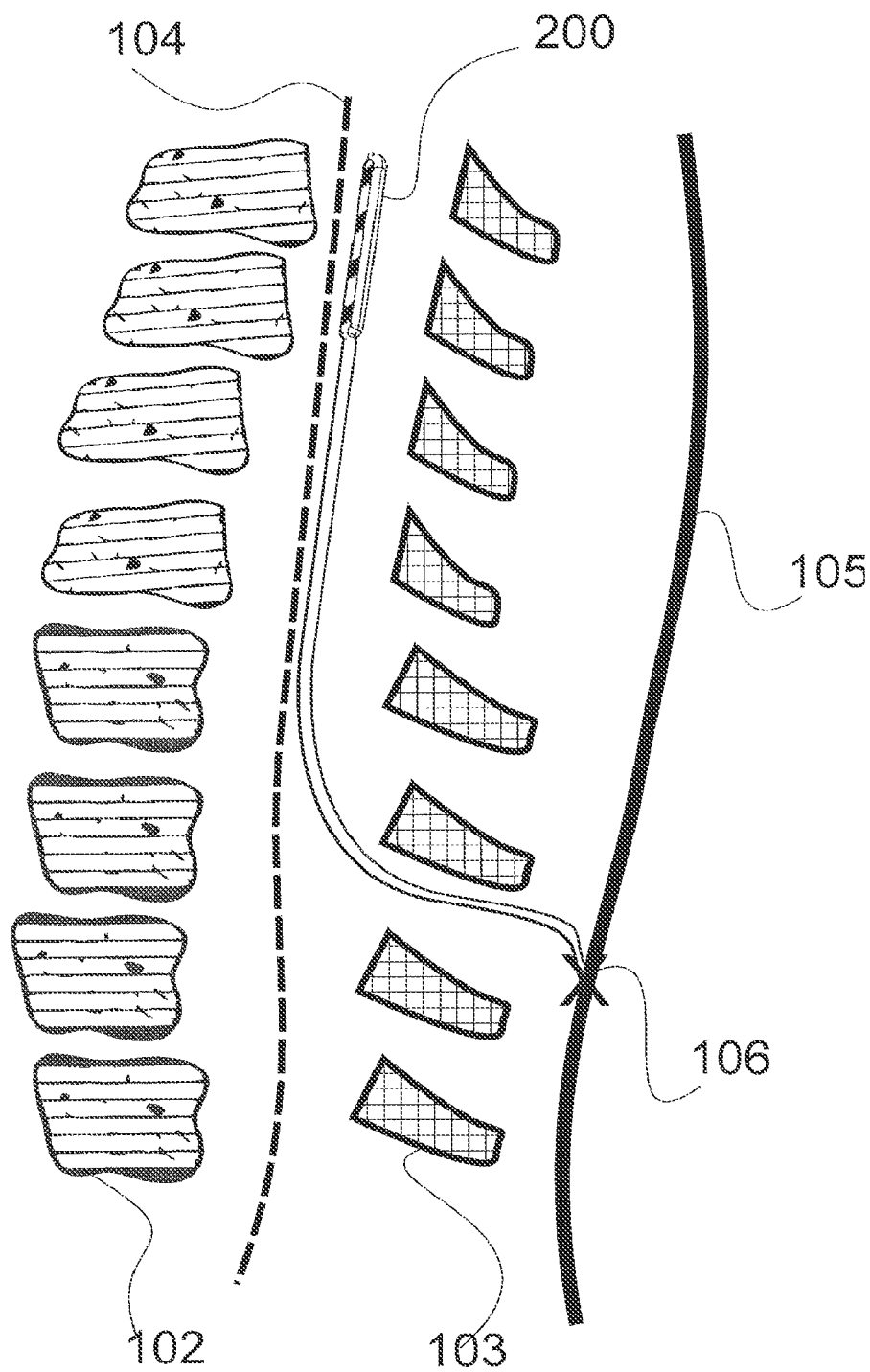
FIG. 3 illustrates a wireless paddle lead in place against the dura of the spinal cord.

FIG. 3 illustrates a wireless paddle lead 200 in place against the dura 104 of the spinal cord after being implanted into the human body for spinal cord stimulation applications. The small incision at the skin 105 can be stitched with a suture or sterile strip after placement of the anchoring mechanism 106. Wireless paddle leads shown here may have electrodes that confine the current path in a direction generally perpendicular to the dura, as will be discussed in association with FIG. 11C. This directionality may be desirable to zero in on a target particular tissue and to reduce electrical charges for efficacious stimulation.

Figure 4A:
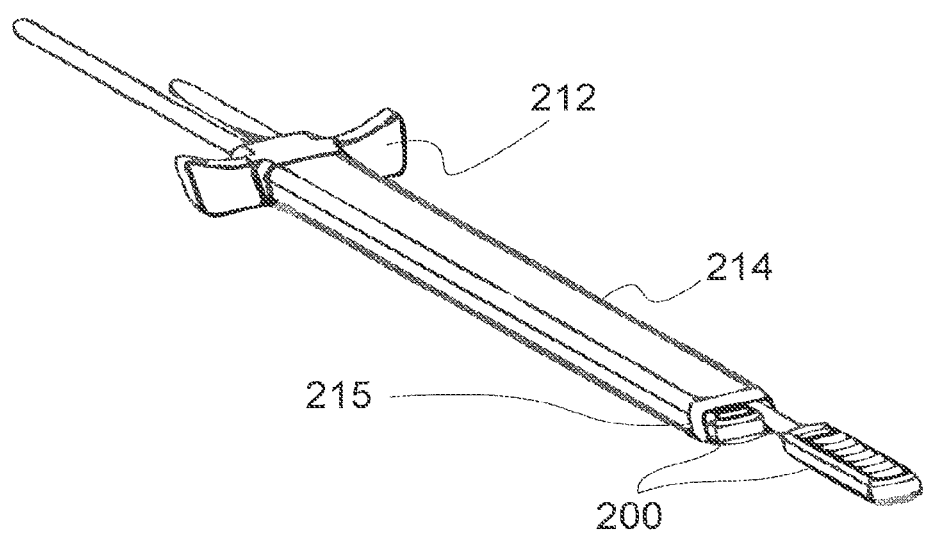
FIG. 4A illustrates an example of an introducer.

FIG. 4A illustrates an example of an introducer 214 that can fit in between two vertebrae without the need for a surgical laminotomy or removal of any bone tissue. The introducer 214 includes a handle 212 for use by the medical staff during the insertion procedure. The width of each handle can be between about 8 mm and about 15 mm. The length of each handle can be between about 10 mm and about 18 mm. The thickness of the handle may be between about 2.5 mm and about 6 mm. The introducer 214 has an inner channel 215 that can house, for example, two wireless paddle leads 200 placed one at a time, sequentially through the same introducer channel. As illustrated, the example wireless paddle lead 200 can have a flat tip.

Figure 4B:
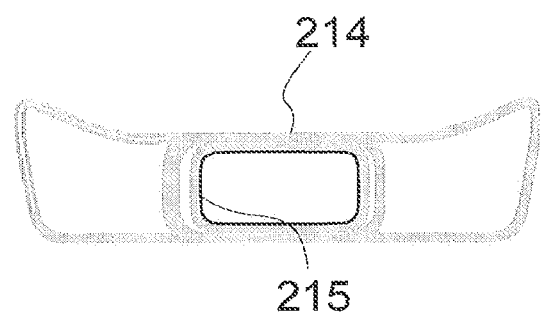
FIG. 4B shows a cross-sectional view of the introducer illustrated in FIG. 4A.

FIG. 4B shows a cross-sectional view of the introducer illustrated in FIG. 4A. This cross-sectional view may also be known as a profile view.

Figure 5A:
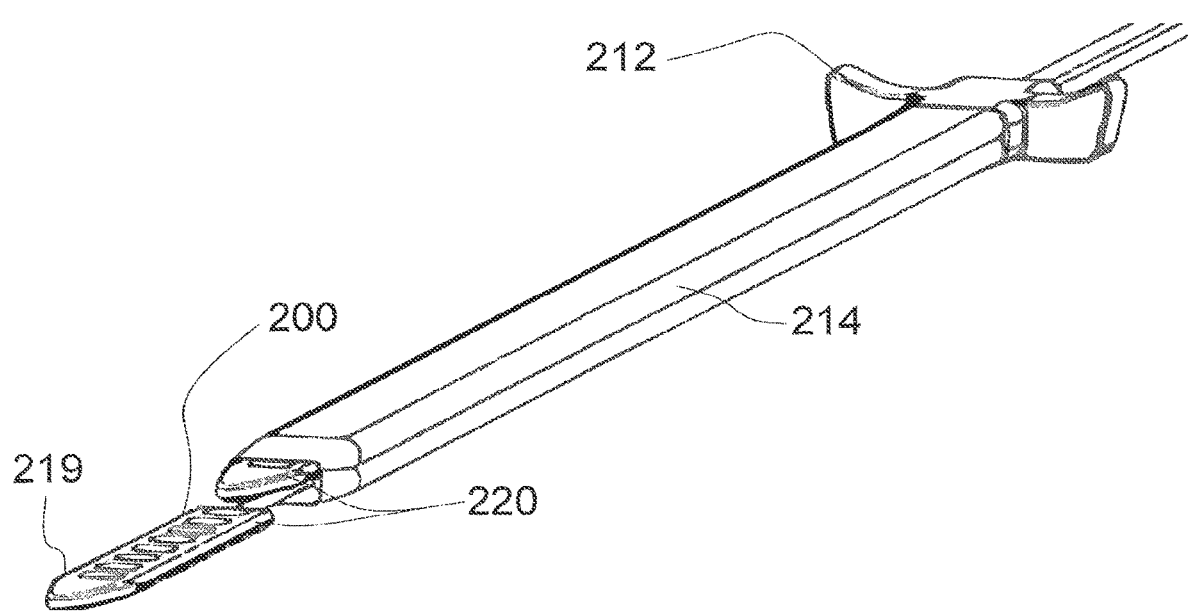
FIG. 5A illustrates another example of an introducer.

FIG. 5A illustrates another example introducer 214 that can fit through the vertebrae without the need for a surgical laminotomy or removal of any bone tissue. The introducer 214 includes a handle 212 for use by the medical staff during the insertion procedure. The introducer 214 has an inner channel 217 that can house, for example, two slim factor wireless paddle leads 220 placed one on top of the other. The two slim factor wireless paddle leads 220 can be stacked vertically in the inner channel 217 at the same time. As illustrated, the example wireless paddle lead 220 can have a pointed tip 219 that aids in directing the paddle lead through the tight epidural space of a smaller patient. The example wireless paddle lead 220 can also have a flat tip that aids in laying the electrode columns parallel with the spine from a fluoroscopic view or rounded tip that aids in both laying the electrode columns parallel with the spine and in directing the paddle lead through the epidural space.

Figure 5B:
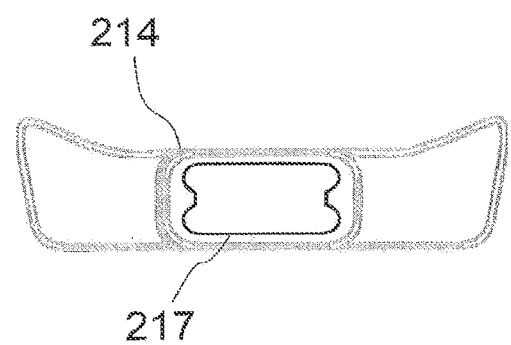
FIG. 5B shows a cross-sectional view of the introducer illustrated in FIG. 5A.

FIG. 5B shows a cross-sectional view of the introducer illustrated in FIG. 5A. This cross-sectional view may also be known as a profile view.

Figure 6A:
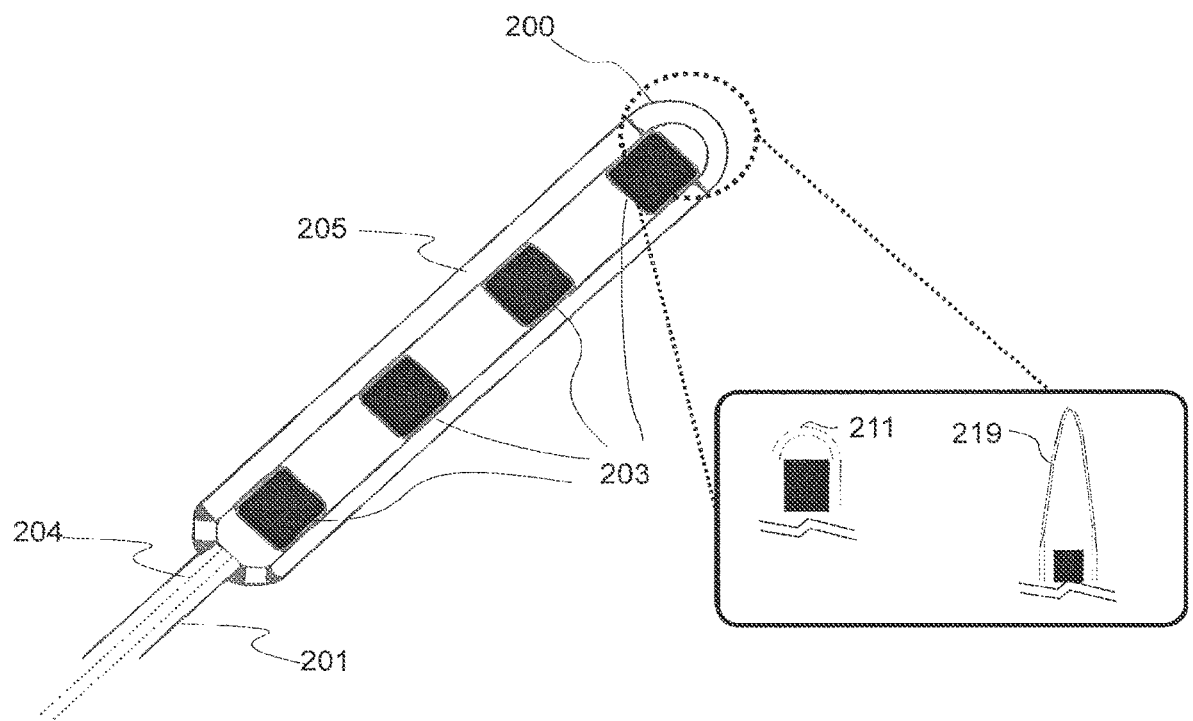
FIG. 6A illustrates the distal tip of a wireless paddle lead.

FIG. 6A illustrates the distal tip of a wireless paddle lead 200. The wireless paddle lead 200 may include, for example, four electrodes 203 and the spacers between the electrodes. The wireless paddle lead 200 can include between two to sixteen electrodes 203 located on the distal end of the lead (not shown). The distal tip may have a height of between about 1.3 mm and about 2.0 mm, and a width between about 2.0 mm and about 4.0 mm. The electrodes 203 may have a longitudinal length between about 1.0 mm and about 6.0 mm from the distal tip toward the proximal tip and a width of between about 0.4 mm and about 3.0 mm. The total electrode surface area of the lead 200 may be between about 0.8 $mm^2$ and about 60.0 $mm^2$. The spacing between the electrodes 203 may be between about 1 mm and about 6 mm from distal to proximal.

The various leads described herein may include anywhere from one to sixteen electrodes, any of which can be designated by the programmer as either a cathode or an anode. For example, electrodes 203 can include multiple cathodes coupled to the targeted tissue as well as at least one anode. The electrode array can receive electrical stimulation waveform pulses ranging from 0 to 10V peak amplitude at a pulse width reaching up to a maximum of 1 millisecond. The polarity of the electrodes can produce various volume conduction distributions from the cathodes to the anodes to inhibit or excite surrounding nerve tissue, which may include A-δ and/or primary or secondary c-fiber afferents. To minimize electrode impedance, the electrodes may be made of a conductive, corrosion resistant, biocompatible material such as, for example, platinum, platinum-iridium, gallium-nitride, titanium-nitride, or iridium-oxide.

Excluding the electrodes 203, which are coupled to the surrounding tissue, the remaining portions of the wireless lead embodiments described herein may be insulated from surrounding body tissue partially or totally by an external coating layer of biocompatible dielectric material with a low dielectric constant. Materials with rigidity similar to that of tissue can be used to reduce the risk of migration and the development of fibrous scar tissue. Such fibrous scar tissue can increase electrode-tissue impedance. If the electrode-tissue impedance can be kept low, less energy may be consumed to achieve stimulation of the targeted tissues.

In certain embodiments, the wireless paddle lead 200 can have a rounded tip 211 at the distal end. Rounded tip 211 can be a non-conductive tip. Rounded tip 211 can have a length of between 0.5 mm and 2.0 mm, and a smooth finish for navigating the lead through the epidural space.

In certain embodiments, the wireless paddle lead 200 can have a pointed tip 219 at the distal end. Pointed tip 219 can be a non-conductive tip. Pointed tip 219 can have a length of between about 2.0 mm and about 6.0 mm. Pointed tip 219 can enhance the steering capability when the wireless paddle 200 is being deployed.

Figure 6B:
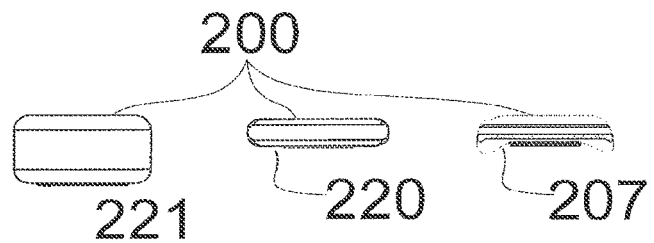
FIG. 6B shows cross-sectional views of the distal ends of three embodiments of a wireless paddle lead.

FIG. 6B shows the cross-sectional views of the distal end of three embodiments of a wireless paddle lead. For example, in certain embodiments, the wireless paddle lead 200 may be a slim factor wireless paddle lead 220. As illustrated in FIG. 6B, the slim factor wireless paddle lead 220 can be thinner than a regular wireless paddle lead 221. For example, slim-factor wireless paddle lead may be between about 1.0 mm and about 1.3 mm in height, which can allow multiple slim-factor wireless paddle leads to be implanted simultaneously or sequentially through an introducer 214. For example, in certain embodiments, wireless paddle leads 200 may be a slim-factor concave wireless paddle lead 207 having a concave profile of between about 1.0 mm and 1.5 mm, concave edges of about 0.2 mm by about 0.3 mm. The concave profile may refer to the height of the slim-factor concave wireless paddle lead 207. The concave edge may refer to the dimension of the concave shape corner the slim-factor concave wireless paddle lead 207. The slim factor concave wireless paddle lead 207 may be placed as close as possible to the dorsal spinal column.

In certain embodiments, at least one additional wireless lead may be placed in parallel or offset with the initial wireless lead. In some embodiments, the wireless leads may be activated sequentially. In other embodiments, wireless leads can be activated simultaneously.

Figure 7A:
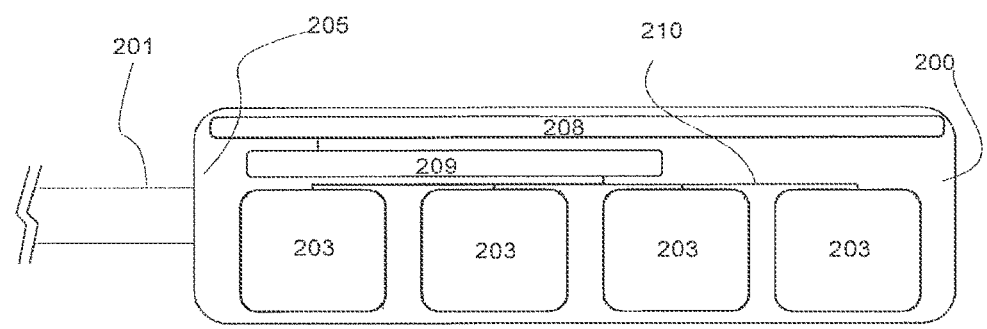
FIGS. 7A and 7B respectively illustrate the dorsal and ventral sides of an embodiment of a wireless paddle lead.
Figure 7B:
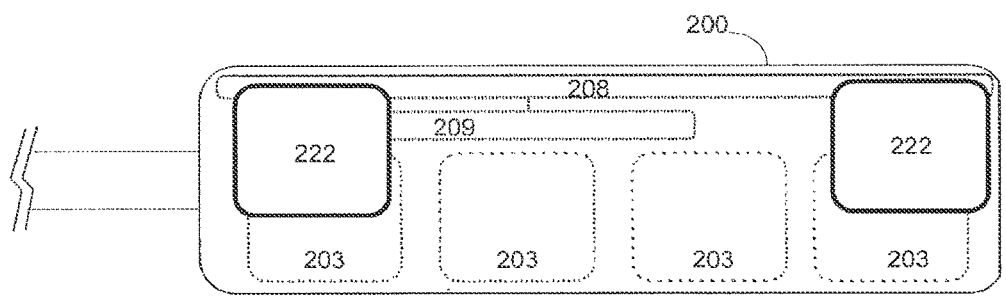

FIGS. 7A and 7B respectively illustrate the dorsal and ventral sides of an implementation of a wireless paddle lead 200. For example, electrodes 203 and between two to eight antenna coupling contacts 222 may be placed on different sides of the wireless paddle lead 200. As discussed in association with FIG. 6A, two to sixteen electrodes 203 can be located on the distal end and embedded into the electrically insulative material 205 of the wireless lead 200.

For example, antenna 208 may be coupled to tissue through the antenna coupling contacts 222 located on the ventral side of the wireless paddle lead 200. The antenna can be, for example, a dipole antenna. Some embodiments may have only one dipole antenna, other embodiments may have multiple antennas of any given length. For example, without limitation, some embodiments may have between two and ten dipole antennas, while other embodiments can have more than ten dipole antennas or more than twenty dipole antennas. In some embodiments, a dipole antenna can range from about 100 microns to about 10 cm in length. In other embodiments, an antenna can consist of any linear dipole configuration ranging from about 20 microns to about 3 mm in thickness. The antenna 208 may also be a folded dipole antenna instead of straight dipole antenna.

Antenna 208 may be configured to receive RF energy from exterior antennas. RF wave propagation energy is divided into two regions, the radiative region and the reactive region. The radiative region is within $2D^2/\lambda$, and the radiated power varies with distance from the antenna. For a short dipole antenna, the reactive component is approximately $\lambda/2\pi$. The induced field for antennas placed in biological tissue is a function of body geometry, tissue properties, and the exposure conditions. The efficiency of the RF waveform inside a lossy media, such as body tissue, is attenuated by the tissue as it propagates. To increase the power efficiency of a small antenna in lossy matter, the dipole antenna configuration can be optimized at high frequencies to minimize losses, such as, for example, from about 800 MHz to 5.8 GHz or greater.

The antenna coupling contacts 222 in certain embodiments may have a longitudinal length between about 1.0 mm and about 6.0 mm from the distal tip toward the proximal tip and a width of between about 1.0 mm to about 2.5 mm. The spacing between the antenna coupling contacts 222 may be between about 30 mm and about 80 mm. The antenna coupling contracts 222 may improve the efficiency of the radiative coupling between internal antenna 208 and the antenna(s) (not depicted) located externally to the body. The antenna coupling contracts 222 may be made of noncorrosive metals, such as, for example, platinum, platinum-iridium, gallium-nitride, titanium-nitride, or iridium-oxide.

Antenna coupling contacts 222 may be connected by conducting wires 210 to the antenna(s) 208 and the waveform conditioning circuit 209. Waveform conditioning circuitry 209 may include, for example electronic components such as, for example diodes, resistors and capacitors. Waveform conditioning circuitry 209 can use the incoming energy to provide a stimulation waveform to the electrodes for excitation of nerve tissue. In some embodiments, frequencies from about 800 MHz to about 5.8 GHz may be received by the implanted antenna 208. The stimulating waveform released into the tissue from electrodes 203 is rectified to provide waveforms at lower frequencies, e.g., at typically from about 5 Hz to about 1000 Hz.

Waveform conditioning circuitry 209 is configured to rectify the waveform signal received by implanted antenna 208. Waveform conditioning circuitry 209 may also have charge balance microelectronics to prevent the corrosion of the electrodes. To minimize reflection of the energy back from the electrodes into the circuitry, waveform-conditioning circuitry 209 may include isolation circuits to block high frequency signals.

Figure 7C:
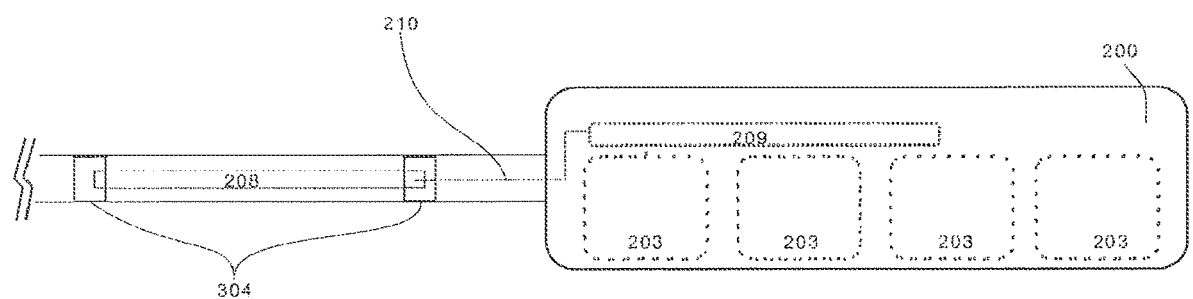
FIG. 7C illustrates the ventral side of another embodiment of the wireless paddle lead.

FIG. 7C illustrates the ventral side of another embodiment of a wireless paddle lead 200, in which the implanted antenna 208 is separated from the distal end 205 of wireless paddle lead 200. In some embodiments, the implanted antenna 208 may be placed remotely from the distal end 205 of the wireless paddle lead 200 and inside a lumen in extension tubing 201 within the lead body. In some embodiments, the implanted antenna 208 may be the extension line of one of the antenna coupling contacts 304. In some embodiments, antenna coupling contacts 304 may be located proximal to the electrodes 203. Antennas 208 may be further connected to the waveform conditioning circuitry 209 via shielded wiring 210. The waveform conditioning circuitry 209 may be directly wired to the electrodes 203 (located on the ventral side).

In some embodiments, the wireless leads described herein may have multiple layers. These layers can include, without limitation, encasing material close to the electrodes with a biocompatible compound that elicits minimal scar tissue formation. In addition, layers may include polymers such as, without limitation, polymethymethacrylate (PMMA), polydimethylsiloxane (PDMS), parylene, polyurethane, polytetrafluoroethylene (PTFE), or polycarbonate. Another layer of a material that may be included contains a small relative permeability and low conductivity located above the antennas 208 to allow for optimal coupling with an exterior antenna (not depicted). Yet another layer can comprise a coating of a silicone elastomer to assist in preventing migration of the wireless lead to the surrounding tissue.

Figure 8:
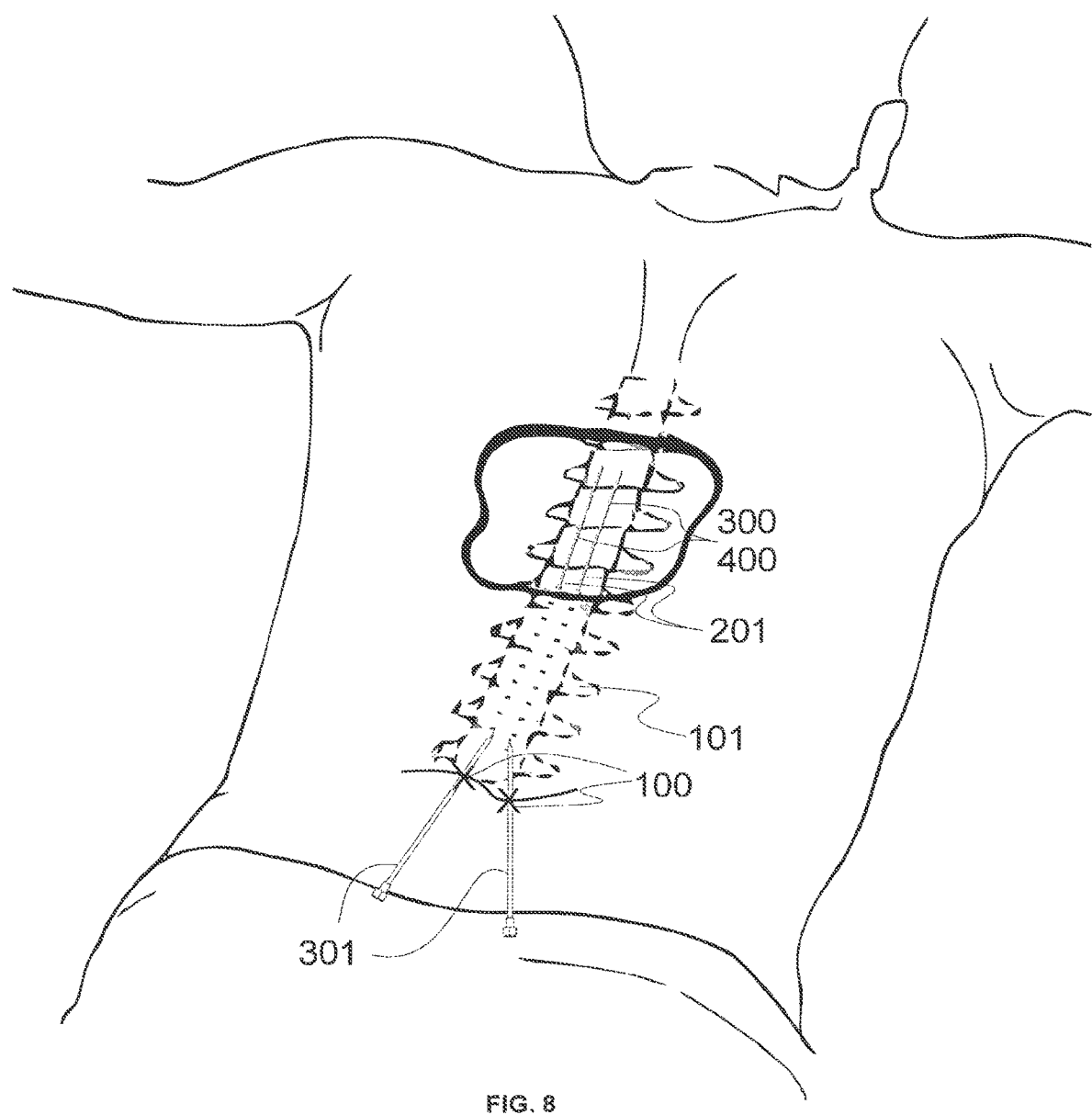
FIG. 8 illustrates an embodiment of a cylindrical and a semi-cylindrical wireless lead being placed in the epidural space using a needle.
Figure 9:
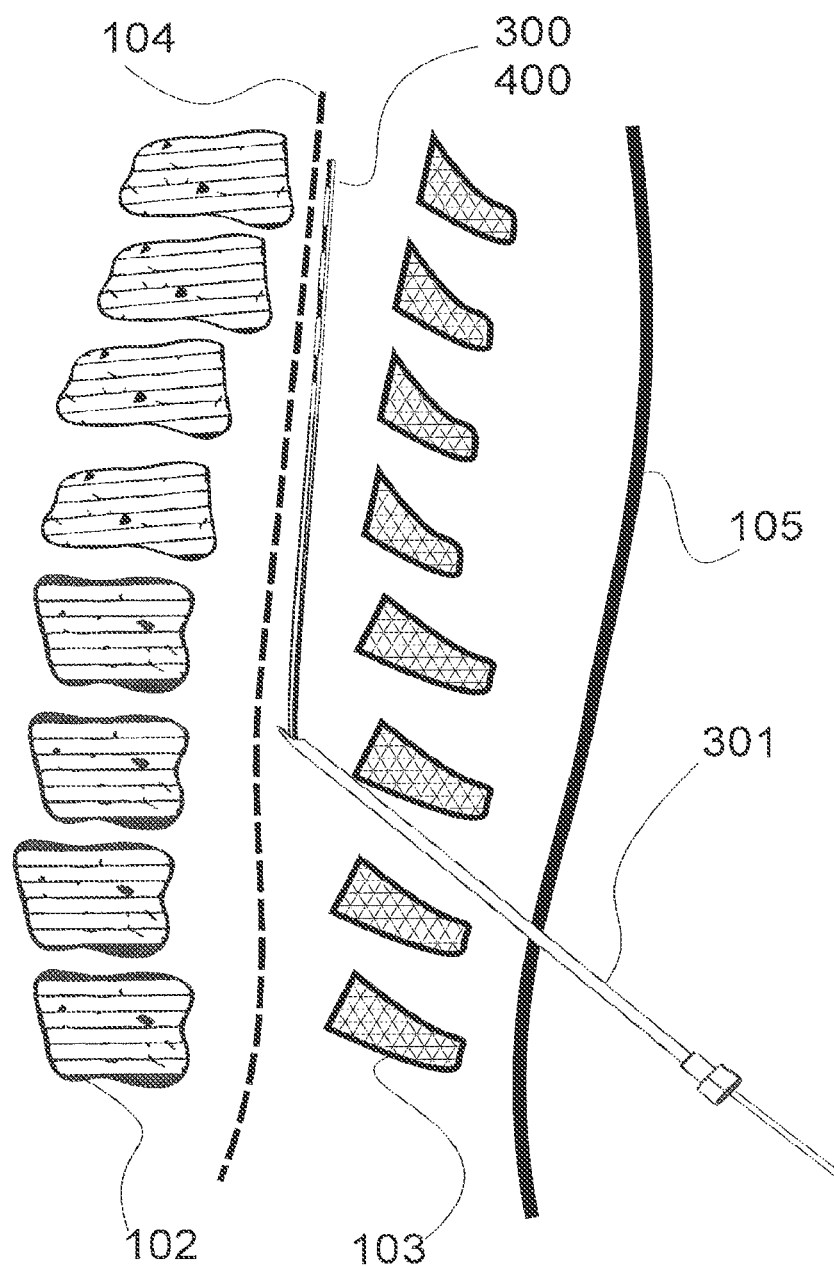
FIG. 9 illustrates an example of a cylindrical or semi-cylindrical wireless lead being implanted in the epidural space using a needle.

FIGS. 8 and 9 illustrates an example of a wireless cylindrical lead 400 or a wireless semi-cylindrical lead 300 being implanted in the epidural space using needles 301. Cylindrical wireless leads may also be referred to as circumferential leads, while semi-cylindrical wireless leads may also be referred to as semi-circumferential or semi-elliptical wireless leads. Wireless cylindrical leads 400 or wireless semi-cylindrical leads 300 can be introduced into the body through needle 301. The needle 301 may be a tuohy needle, 14-Gauge, or smaller (for example, 22 Gauge). Alternatively, the wireless leads 300 and 400 in may be introduced into the epidural space through an introducer 202 (see, for example, FIG. 1). Introducers 202 or needle 301 may be inserted through the outer skin of the body through a small incision in the skin 105 and in between the vertebrae 103 at no more than a 45-degree angle, lateral to the spinous processes off the midline, and placed against the dura 104 of the spinal column 102 to lie perpendicularly to the spinal cord. The wireless leads 300 or 400 can contain extension tubings 201 that terminate just under the entry point 100 of the skin. The wireless lead may be guided upwards in the epidural space according to the angle of introducer or needle insertion. After the wireless lead has been placed, a subcutaneous anchor is used to stop vertical and horizontal migration of the wireless lead.

Figure 10:
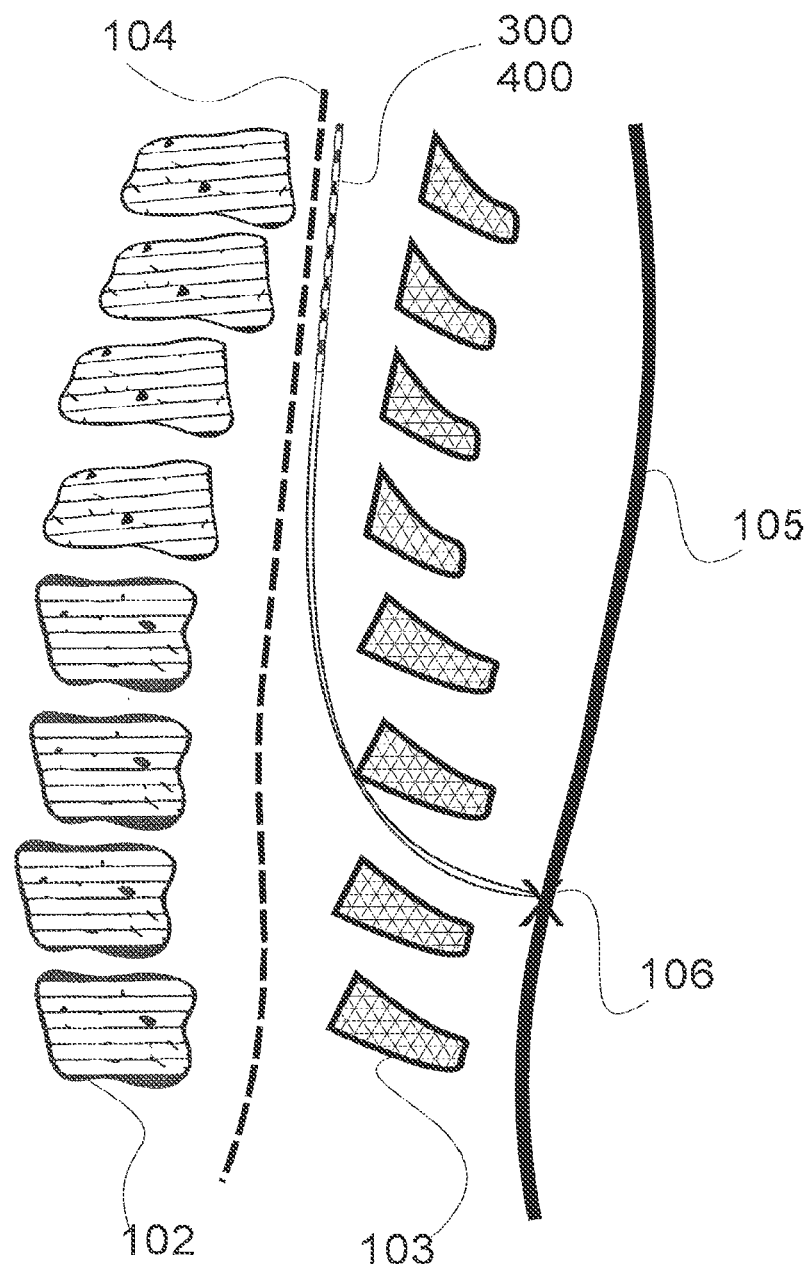
FIG. 10 illustrates a cylindrical or semi-cylindrical wireless lead placed against the dura in the spinal column.

FIG. 10 illustrates embodiments of a cylindrical wireless lead 300 or semi-cylindrical wireless lead 400 after being implanted. A cylindrical 300 or semi-cylindrical 400 wireless lead may be placed against the dura 104 of the spinal cord and the small incision at the skin 105 is stitched with a suture or sterile strip after placement of the anchoring mechanism 106.

Figure 11A:
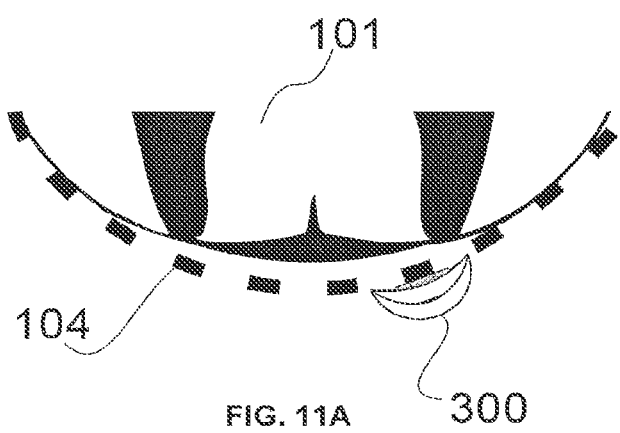
FIG. 11A-11C illustrate cross-sectional views of a semi-cylindrical lead, a cylindrical lead, and a paddle lead, respectively, while those leads are placed against the dura.
Figure 11B:
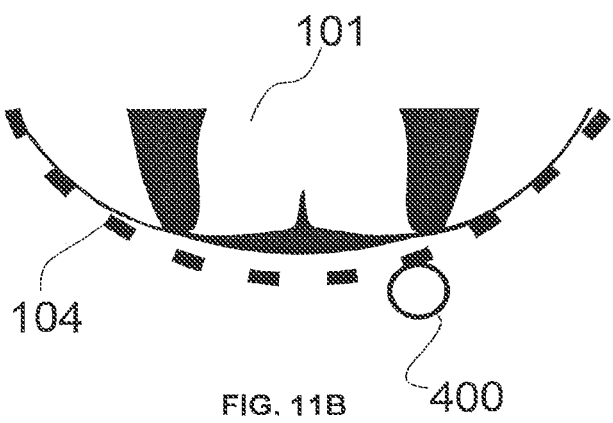
Figure 11C:
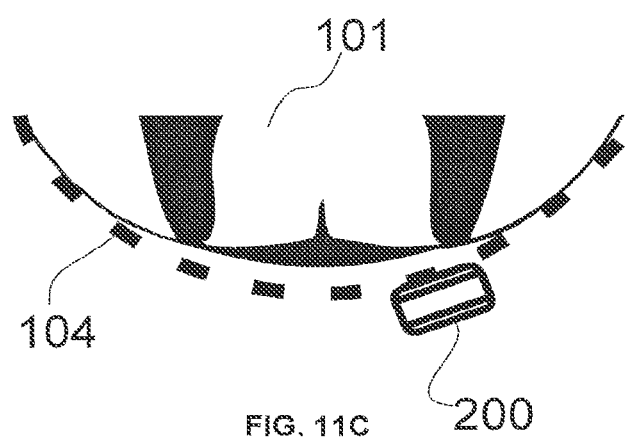

FIG. 11A-11C respectively illustrate the cross-sectional views of the placement of a wireless semi-cylindrical lead 300, a wireless cylindrical lead 400, and a wireless paddle lead 200 after successful implantation in relation to the dura 104 of the spinal cord 101.

Figure 12A:
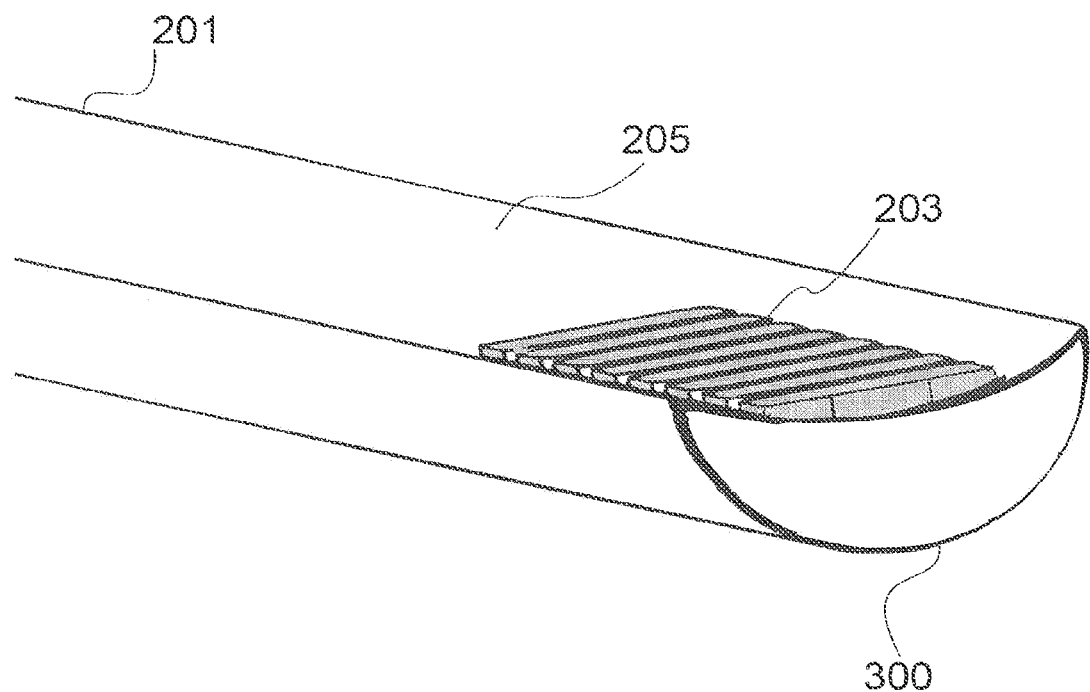
FIGS. 12A-12B illustrate perspective and profile views, respectively, of an embodiment of a wireless semi-cylindrical lead.

FIG. 11A shows the placement of a wireless semi-cylindrical lead 300 relative to the dura 104 of the spinal cord 101. The wireless semi-cylindrical (also referred to as half-circumferential or half-elliptical) lead 300 may have electrodes that are straight, as depicted in FIG. 12A, or that are concave and half-cylindrical in shape. Semi-cylindrical electrodes can match the shape of the enclosure. The semi-cylindrical shape of the enclosure of lead 300 may help the lead to mechanically conform to the contour of the spinal column 102. The shape of the enclosure can also assist in targeting the electrical volume conduction inward towards the dura 104, and avoid radiating energy outwards towards the ligaments, vertebrae and skin (non-excitable tissue). More generally, the conducting field generated by the electrodes is uni-directional in nature because the conducting field culminates mainly in the enclosure and electrode faces are pointed in one direction. By removing the unnecessary emission from over 270 degrees of a cylindrical electrode (see, for example, in FIGS. 14B and 15) radiating towards non-excitable tissue, the semi-cylindrical wireless lead 300 can reduce the amount of energy required for a successful stimulation. Therefore, the benefits of the example semi-cylindrical wireless lead 300 may include the directional delivery of stimulation energy as confined by the shape of the electrode.

FIG. 11B shows the placement of a wireless cylindrical lead 400 relative to the dura 104 of the spinal cord 101 after successful implantation. As depicted, the wireless cylindrical lead 400 is placed against dura 104.

Figure 12B:
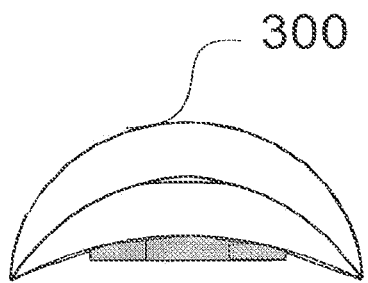

FIG. 11C shows the placement of a wireless paddle lead 200 relative to the dura 104 of the spinal cord 101 after successful implantation. As depicted, the wireless paddle lead 200 is placed against dura 104. Wireless paddle lead 200 may have electrodes that confine the current path in a direction generally perpendicular to the dura. This directionality may be desirable to zero in on a target particular tissue and to reduce electrical charges for efficacious stimulation FIGS. 12A and 12B illustrate perspective and profile views, respectively, of an implementation of a wireless semi-cylindrical lead 300. The semi-cylindrical lead 300 can have, in certain embodiments between two to sixteen electrodes 203 at the distal end 205, each with a diameter typically between about 0.8 mm and about 1.4 mm, and concave ventral aspects with bend radiuses typically between about 0.6 mm and about 3.0 mm. The electrodes 203 may have longitudinal lengths between about 1.0 mm and about 6.0 mm from the distal tip towards the proximal tip with widths typically between about 0.4 mm and about 1.0 mm. The total electrode surface area of the wireless lead 300 is typically between about 0.8 mm$^2$ and about 60.0 mm$^2$. The spacing between the electrode contacts is typically between about 1.0 mm and about 6.0 mm. The distal tip of the lead body may be a non-conductive tip that is pointed with a length of between about 0.5 mm and about 2.0 mm, and a smooth finish for navigating the lead through the epidural space.

Figure 13A:
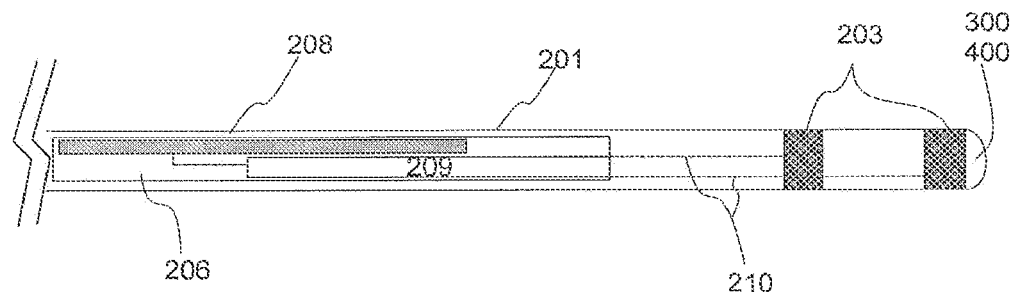
FIG. 13A-13C variously illustrate the electronic components included in two embodiments of the wireless lead.
Figure 13B:
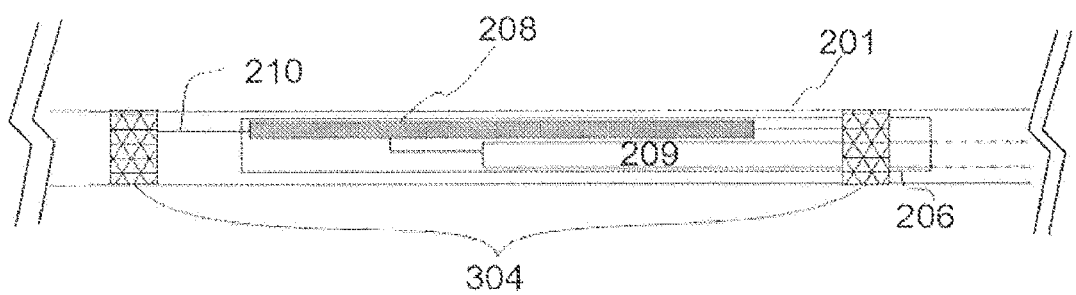
Figure 13C:
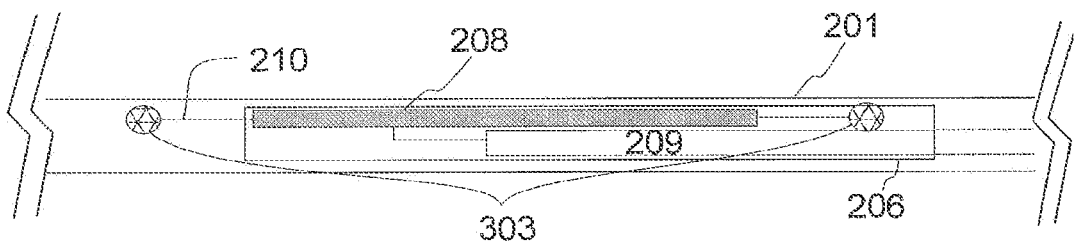

The wireless semi-cylindrical lead 300 may include between two to eight antenna coupling contacts 304, as illustrated in association with FIG. 7C, that are wired to the implanted antenna(s) 208 and the flexible circuits 206 (as illustrated in association with FIGS. 12 and 13). The antenna coupling contacts 304 may be proximal of the electrodes 203. The antenna coupling pads 304 may have a longitudinal length of between about 1 mm and about 6 mm from the distal tip to the proximal tip. The spacing between the antenna coupling contacts 304 is typically between 30 mm and 80 mm. In some embodiments, small antenna coupling contacts 303, to be discussed in association with FIG. 13C, may be used. Antenna coupling contacts 303 may have a diameter between about 0.2 mm and about 0.6 mm.

Embodiments of wireless leads described herein can have a larger surface area directed towards the dura mater than existing percutaneous leads. This increased surface area can lower the tissue to electrode impedance values and can lead to larger currents for stimulation.

FIGS. 13A-13C variously illustrate electronic components included in two different embodiments of the wireless lead, namely, a wireless semi-cylindrical lead 300 and a wireless cylindrical lead 400.

FIG. 13A shows an example wireless lead (e.g. a wireless semi-cylindrical lead 300 or a wireless cylindrical lead 400) with extension tubing 201. The tubing 201 may house electrodes 203, implanted antenna 208, waveform conditioning circuitry 209, and wires 210. As discussed above in association with FIGS. 7A-7B, the waveform conditioning circuitry 209 can include components for rectifying the received RF energy and for charge balancing the waveform for tissue stimulation.

One or more flexible circuits 206 may be used to carry various parts of the electronic components. For instance, the flexible circuits 206 may include the waveform conditioning circuitry 209 and implantable antenna(s) 208. The flex circuit may also include portions of the wires 210, which connect the electronics, such as circuitry 209, to the electrodes 203. The flexible circuits 206 may be between about 15 mm and about 90 mm long, and about 0.7 mm and about 2.0 mm wide. The total height of the flexible circuit 206 with the waveform conditioning circuitry 209 may be between about 0.2 mm and about 0.4 mm. The flexible circuit 206, when placed inside of the cylindrical wireless lead 400 may undergo a bend radius under about 0.5 mm. As illustrated in FIG. 13A, in some embodiments, the flexible circuit 206 may contain a conductive trace to act as an antenna 208.

FIG. 13B shows another example of a wireless lead (e.g. a wireless semi-cylindrical lead 300 and a wireless cylindrical lead 400) encapsulated that includes tubing 201. The tubing houses antenna(s) 208 and the waveform conditioning circuitry 209, both of which may be formed on a flex circuit 206 similar to the flex circuit described with respect to FIG. 13A. At least a portion of the wires 210 may be formed on the flex circuit as well. Wires 210 connect, for example, the circuitry 209 to the electrodes (not shown in FIG. 13B). Wires 210 also connect the antenna 208 to tissue exposed ring antenna coupling contacts 304. Tissue exposed ring antenna coupling contacts 304 can be circumferential rings with outer diameter between about 0.8 mm and about 1.4 mm, and longitudinal lengths between about 0.5 mm and about 6.0 mm.

FIG. 13C shows yet another example wireless lead (e.g. a wireless semi-cylindrical lead 300 and a wireless cylindrical lead 400) with extension tubing 201. The extension tubing 201 houses antenna(s) 208 and the waveform conditioning circuitry 209, both of which may be formed on a flex circuit 206 similar to the flex circuit described with respect to FIG. 13A. At least a portion of the wires 210 may be formed on the flex circuit as well. Wires 210 connect, for example, the circuitry 209 to the electrodes (not shown in FIG. 13C). Wires 210 also connect the antenna 208 to tissue exposed small antenna coupling contacts 303. Tissue exposed small antenna coupling contacts 303 may be made of a conductive cylindrical piece of metal of diameter between about 0.2 mm and about 0.6 mm and thickness of between about 0.2 mm and about 0.6 mm. Tissue exposed small antenna coupling contacts 303 may contact tissue and can be embedded into the electrically insulative material 205.

Figures 14A, 14B:
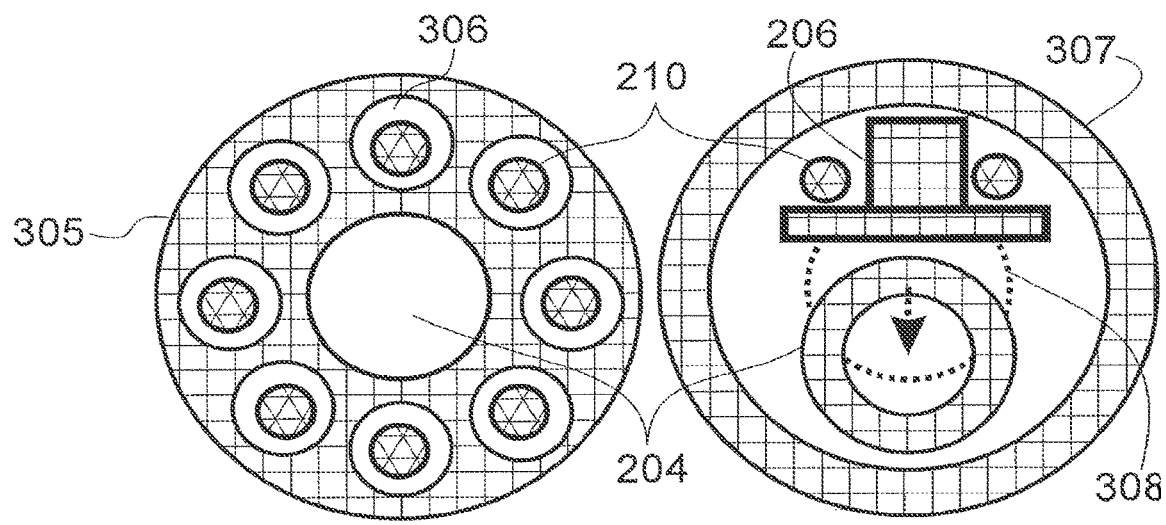
FIG. 14A-14B illustrate a cross-sectional view of a fully cylindrical wireless lead or a semi-cylindrical wireless lead.

FIG. 14A illustrates a cross-sectional view of an embodiment of a fully cylindrical wireless lead 400 or a semi-cylindrical wireless lead 300 at a position proximal to the distal tip. The embodiment shown is a multi-lumen extrusion 305 having a center lumen 204 and multiple orbital lumens 306 (for example, one to ten or more). The multi-lumen extrusion 305 may be proximal to the single-lumen extrusion 307, shown in the right graph, on one wireless lead (for example, a fully cylindrical wireless lead 400 or a semi-cylindrical wireless lead 300). The multi-lumen extrusion 305 may act as backbone for guiding the conducting wires 210, housed in side lumens 306, and a stylet (as discussed in association with FIG. 1) placed through the center lumen 204. The multi-lumen plastic extrusion 305 can be made up of between one to ten or more orbital lumens 306, each with inner diameters of between about 0.1 mm and about 0.6 mm. The multi-lumen plastic extrusion 305 may have an outer diameter of between about 0.8 mm and about 1.4 mm. In certain embodiments, the multi-lumen extrusion 305 may be ablated (i.e., heated to be deformed) to a final outer diameter of between about 0.6 mm and about 0.9 mm which allows the extrusion 305 to connect male to female into a single lumen extrusion 307, as shown in the right graph. A navigation stylet may be placed inside the inner lumen 204 to guide the wireless lead into the epidural space. The inner lumen 204 maintains a clear channel without obstruction and may be fused with the single lumen extrusion 307 at the interconnection between extrusions 305 and 307 and after the above-mentioned ablation.

FIG. 14B illustrates a cross-sectional view of another embodiment of a fully cylindrical wireless lead 400 or a semi-cylindrical wireless lead 300 at a position proximal to the distal tip. This embodiment is a single-lumen extrusion 307, which may have inner diameter of between about 0.3 mm and about 1.4 mm. The single lumen extrusion 307 may be pulled around the outside of, for example, the wireless semi-cylindrical lead 300 and heat formed to match an outer diameter of between about 0.8 mm and about 1.4 mm. The single lumen extrusion 307 can leave sufficient empty space for the flexible circuit 206 to be encapsulated inside. The inner lumen 204 may be offset by a distance indicated by 308 inside the single lumen 307 to provide a gap space for the flexible circuit 206. Conducting wires 210 from the side lumens 306 may connect to terminal features (not depicted) on the flexible circuit 206. The gap space inside the single-lumen extrusion 307 between the flexible circuit 206 and inner lumen 204 may be back-filled with a biocompatible polymer to give added rigidity for protecting the flexible circuit components 206 and conducting wires 210.

Figure 14C:
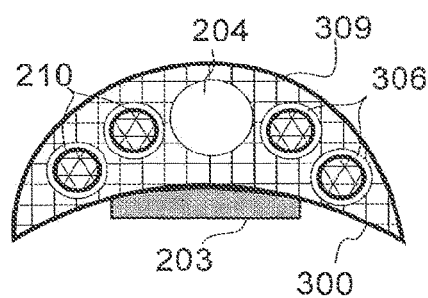
FIG. 14C illustrates a cross-sectional view towards the distal end of a semi-cylindrical wireless lead.

FIG. 14C illustrates a cross-sectional view towards the distal end of a semi-cylindrical wireless lead 300. For a semi-cylindrical wireless lead 300, the concave multi-lumen extrusion 309 may house the conducting wires 210 running from the flex circuit 206 to the electrodes 203. The concave shape of multi-lumen extrusion 309 may allow semi-cylindrical wireless lead 300 to conform to the curvature of the spinal cord. The bend radius of the concave dorsal aspect is between about 0.6 mm and about 3.0 mm. The concave multi-lumen extrusion 309 may contain between one and ten or more orbital lumens 306 acting as channels for conducting wires and a central lumen 204 for the stylet. The lumens 204 and 306 may have inner diameters of between 0.1 mm and 0.6 mm. The orbital lumens 306 may be drilled into from the dorsal side during manufacturing to create channels to connect the conducting wires 210 to the electrodes 203.

Figure 15:
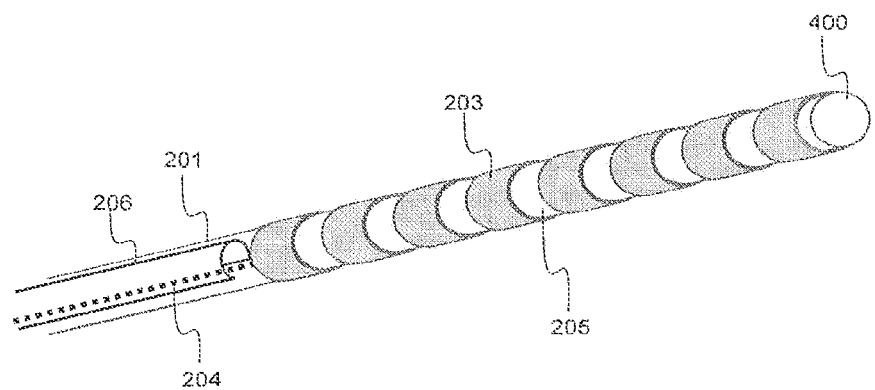
FIG. 15 illustrates an embodiment of a cylindrical wireless lead.

FIG. 15 illustrates an example of a fully circumferential wireless lead. The cylindrical wireless lead 400 may have between two and sixteen cylindrical electrodes 203 on its distal end with a diameter between about 0.8 mm and about 1.4 mm for epidural spinal cord stimulation applications. The electrodes 203 may have a longitudinal length of between about 1.0 mm and about 6.0 mm from the distal tip toward the proximal tip. The spacing between the electrode contacts may be between about 1.0 mm and about 6.0 mm. The total electrode surface area of the cylindrical wireless lead body 400 may be between about 1.6 $mm^2$ and about 60.0 $mm^2$. The distal tip of the cylindrical wireless lead body 400 may be a non-conductive tip that is rounded with a length of between about 0.5 mm and about 1.0 mm, with a smooth finish for navigating the lead through the epidural space. Between two to eight tissue exposed ring antenna coupling contacts 304 may be proximal to the electrodes 203. The tissue exposed circular antenna coupling contacts 304 may have a longitudinal length of between about 1.0 mm and about 6.0 mm from the distal tip toward the proximal tip. The spacing between the tissue-exposed circular antenna coupling contacts 304 may be between about 30 mm and about 80 mm. In certain embodiments, tissue exposed small antenna coupling contacts 303 with a diameter between about 0.2 mm and about 0.6 mm may be used in lieu of the illustrated tissue exposed small antenna coupling contacts 303. Extension tubing 201, as discussed in association with FIGS. 1, 7C, 8 and 9, can provide an enclosure that houses, for example, flex circuitry 206. Flex circuitry 206 has been discussed in association with FIGS. 13A to 13C. Extension tubing 201 may include a center lumen 204. As discussed in association with FIG. 14A, a stylet can be placed through center lumen 204 to provide guidance during implantation of lead 400 into, for example, through a lumen in to a human body.

Various implementations of the technology may allow placement of wireless lead in the epidural space, between the dura mater and arachnoid membranes, or subdurally in the intrathecal space, where significant reactions and scarring would be minimized. Insertion in any of these locations may be done by injecting the device from a smaller gauge needle (e.g., 14 to 22-gauge needle or out of a cannula steered to the proper position by a removable stylet). In some implementations, once in position, no further skin incisions or placement of extensions, receivers or implanted pulse generators are needed. Various implementations of the wireless neural modulation system may have significant advantages due to the small size and lack of extension wires for transfer of energy, allowing placement with minimal trauma and long term effective therapy in places where larger implantable devices could cause more scar tissue and tissue reactions that may affect efficacy and safety.

A number of implementations have been described. Nevertheless, it will be understood that various modifications may be made. Accordingly, other implementations are within the scope of the following claims.

What is claimed is:

1. An implantable neural stimulator comprising:
   one or more electrodes configured to apply one or more stimulation pulses to a neural tissue;
   an antenna configured to receive, wirelessly and through electrical radiative coupling, an input signal containing electrical energy; and
   a circuit coupled to the antenna and the one or more electrodes, wherein the circuit is configured to:
     apply the electrical energy contained in the input signal to create the one or more stimulation pulses suitable for stimulating the neural tissue; and
     supply the one or more stimulation pulses to the one or more electrodes.

2. The implantable neural stimulator of claim 1, wherein the implantable neural stimulator is packaged to fit inside an introducer or a needle having a diameter no larger than gauge 13.

3. The implantable neural stimulator of claim 2, wherein the implantable neural stimulator comprises an enclosure that includes a lumen configured to accommodate a navigating stylet when the enclosure is inserted into the introducer or the needle.

4. The implantable neural stimulator of claim 3, wherein the enclosure is sized and shaped for delivery into an epidural space of a patient.

5. The implantable neural stimulator of claim 4, wherein the enclosure has a concave shape configured to secure a lateral position on the neural tissue after the implantable neural stimulator has been implanted inside the patient.

6. The implantable neural stimulator of claim 5, wherein the lateral position is with regard to a dorsal aspect of a spinal cord column of the patient.

7. The implantable neural stimulator of claim 3, wherein the enclosure comprises a rounded distal tip or a pointed distal tip.

8. The implantable neural stimulator of claim 3, wherein the enclosure further comprises at least one orbital lumen.

9. The implantable neural stimulator of claim 8, wherein the lumen is located in a single-lumen extension tubing, the at least one orbital lumen are located in an extension tubing, and wherein the extension tubing is located more proximally than the single-lumen extension tubing.

10. The implantable neural stimulator of claim 9, wherein the enclosure further encloses a plurality of antenna coupling contacts, wherein the antenna coupling contacts are electrically coupled to the antenna and the circuit.

11. The implantable neural stimulator of claim 10, wherein the antenna coupling contacts comprise 2 to 8 antenna coupling pairs located proximal to the electrode within the enclosure.

12. The implantable neural stimulator of claim 10, wherein the antenna coupling contacts are connected by conducting wires to the antenna and the circuit, wherein each of the conducting wires is enclosed in a respective orbital lumen.

13. The implantable neural stimulator of claim 1, wherein the electrodes are directionally configured to direct a current associated with the one or more stimulation pulses in a direction that is substantially perpendicular to the neural tissue.

14. The implantable neural stimulator of claim 1 wherein the one or more electrodes comprise a cylindrical or semi-cylindrical array of electrodes.

15. The implantable neural stimulator of claim 1, wherein the circuit comprises: one or more diodes, one or more resistors, and one or more capacitors.

16. The implantable neural stimulator of claim 15, wherein the circuit further comprises: charge balance circuitry, and isolation circuitry.

17. The implantable neural stimulator of claim 15, wherein the circuit is sufficiently flexible to bend over a radius of under 0.5 mm.

18. The implantable neural stimulator of claim 15, wherein the circuit is placed proximal, relative to the electrodes.

19. The implantable neural stimulator of claim 1, wherein the antenna comprises a conductive trace.

20. The implantable neural stimulator of claim 1, wherein the antenna comprises a conductive wire.

* * * * *